United States Patent
Hajime et al.

(10) Patent No.: US 11,065,354 B2
(45) Date of Patent: *Jul. 20, 2021

(54) POST-STEAM STERILIZATION MOISTURE-INDICATING ARTICLES

(71) Applicant: 3M INNOVATIVE PROPERTIES COMPANY, St. Paul, MN (US)

(72) Inventors: Evan K. L. Y. Hajime, Woodbury, MN (US); Myungchan Kang, Woodbury, MN (US); Timothy J. Nies, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 728 days.

This patent is subject to a terminal disclaimer.

(21) Appl. No.: 14/775,745

(22) PCT Filed: Mar. 7, 2014

(86) PCT No.: PCT/US2014/021995
§ 371 (c)(1),
(2) Date: Sep. 14, 2015

(87) PCT Pub. No.: WO2014/150048
PCT Pub. Date: Sep. 25, 2014

(65) Prior Publication Data
US 2016/0022853 A1    Jan. 28, 2016

Related U.S. Application Data

(60) Provisional application No. 61/792,291, filed on Mar. 15, 2013.

(51) Int. Cl.
*A61L 2/28*    (2006.01)
*G01N 31/22*    (2006.01)
(Continued)

(52) U.S. Cl.
CPC .............. *A61L 2/28* (2013.01); *A61B 50/30* (2016.02); *A61L 2/07* (2013.01); *G01N 31/222* (2013.01)

(58) Field of Classification Search
CPC .. A61L 2/28; A61L 2/07; A61B 50/30; G01N 31/222; G01N 21/81
See application file for complete search history.

(56) References Cited

U.S. PATENT DOCUMENTS 3,034,282 A    5/1962  Nathason
4,094,642 A *  6/1978  Sumimoto ................ A61L 2/28
                                                    116/206
(Continued)

FOREIGN PATENT DOCUMENTS

CA       2812577      10/2013
DE      689 12 237    8/1994
(Continued)

OTHER PUBLICATIONS

Clement, L.; "Wet pack problem-solving for rigid sterilization containers"; Healthcare Purchasing News; vol. 29, Issue 7; 2005; pp. 42-44.
(Continued)

*Primary Examiner* — Anthony D Stashick
*Assistant Examiner* — Blaine G Neway
(74) *Attorney, Agent, or Firm* — Qiang Han

(57) ABSTRACT

Post-steam sterilization wet pack indicators are described. The indicators generally comprise a moisture-impermeable layer having a first surface and a moisture-indicating layer comprising a reversible colorimetric steam-sterilization-compatible moisture-indicating medium. The moisture-indicating layer is disposed on or near the first surface of the moisture-impermeable layer. The area of the moisture-indicating layer is dimensionally smaller than the moisture-
(Continued)

impermeable layer such that the edges of the moisture-impermeable layer extend beyond the edges of the moisture-indicating layer. Articles and packages comprising wet pack indicators are also described.

13 Claims, 2 Drawing Sheets

(51) Int. Cl.
A61L 2/07 (2006.01)
A61B 50/30 (2016.01)

(56) References Cited

U.S. PATENT DOCUMENTS

| | | | |
|---|---|---|---|
| 4,302,500 A * | 11/1981 | Flora | A61B 17/085 |
| | | | 156/230 |
| 4,382,063 A * | 5/1983 | Romito | G01N 31/226 |
| | | | 116/207 |
| 4,738,674 A | 4/1988 | Todd et al. | |
| 4,990,284 A | 2/1991 | Lauterbach | |
| 5,008,078 A | 4/1991 | Yaginuma et al. | |
| 5,057,434 A * | 10/1991 | Prusik | B65D 79/02 |
| | | | 116/207 |
| 5,122,451 A | 6/1992 | Tanaka et al. | |
| 5,224,373 A * | 7/1993 | Williams | G01N 31/222 |
| | | | 73/29.02 |
| 5,422,276 A | 6/1995 | Colvin | |
| 5,620,656 A * | 4/1997 | Wensky | A61L 2/28 |
| | | | 116/209 |
| 6,287,518 B1 * | 9/2001 | Ignacio | A61L 2/28 |
| | | | 116/206 |
| 6,534,006 B2 * | 3/2003 | Hehenberger | A61L 2/28 |
| | | | 116/206 |
| 6,649,804 B2 | 11/2003 | Eakin | |
| 6,905,763 B2 | 6/2005 | Crandall et al. | |
| 7,098,253 B2 | 8/2006 | Rasmussen et al. | |
| 7,247,493 B2 * | 7/2007 | Kopelman | G01N 31/221 |
| | | | 422/501 |
| 7,553,450 B2 * | 6/2009 | Attar | G01N 21/81 |
| | | | 116/200 |
| 7,674,835 B2 | 3/2010 | Rasmussen et al. | |
| 7,683,100 B2 | 3/2010 | Rasmussen et al. | |
| 10,119,918 B2 * | 11/2018 | Kang | B01J 20/223 |
| 2002/0000184 A1 | 1/2002 | Paton et al. | |
| 2011/0076416 A1 * | 3/2011 | Klipp | C08G 77/06 |
| | | | 427/487 |

FOREIGN PATENT DOCUMENTS

| | | |
|---|---|---|
| DE | 102 13 066 | 8/2003 |
| EP | 2 320 226 | 5/2011 |
| GB | 284120 | 1/1928 |
| GB | 1466626 | 3/1977 |
| JP | H-0717582 | 1/1995 |
| WO | WO 1993/03774 | 3/1993 |
| WO | WO 98/16821 | 4/1998 |
| WO | WO 2007/081972 | 7/2007 |
| WO | WO 2012/154314 | 11/2012 |
| WO | WO 2013/147934 | 10/2013 |
| WO | WO 2014/078088 | 5/2014 |

OTHER PUBLICATIONS

MacKenzie, K.J.D. et al.; "Inorganic Polymers (geopolymers) containing acid-base indicators as possible colour-change humidity indicators"; Materials Letters; vol. 63; 2009; pp. 230-232.
Rutala, W.A. et al.; "Guideline for Disinfection and Sterilization in Healthcare Facilities, 2008"; CDC; pp. 1-158; see pp. 74.
Training Manual for Health Care Central Service Technicians—American Society for Healthcare Central Service Professionals of the American Hospital Association. Fifth Edition; Jossey-Bass publisher; 2006; Ch. 7, pp. 162-163.

* cited by examiner

POST-STEAM STERILIZATION MOISTURE-INDICATING ARTICLES

CROSS REFERENCE TO RELATED APPLICATIONS

This application is a national stage filing under 35 U.S.C. 371 of PCT/2014/021995, filed Mar. 7, 2014, which claims priority to U.S. Provisional Patent Application No. 61/792,291, filed Mar. 15, 2013, the disclosure of which is incorporated by reference in its entirety herein.

FIELD

The present disclosure relates to articles and packages using moisture indicators for detection of wet packs following steam sterilization.

BACKGROUND

Within the Central Sterilization (CS) Department of a hospital, medical instruments are cleaned, assembled, processed, packaged, stored, and issued for patient care. Medical instrumentation is received from the Operating Room into the decontamination area of the CS Department. There, instruments are manually washed and disinfected and visually assessed for cleanliness before placing in an automatic washer-disinfector. Once processed in a washer-disinfector, instruments are visually examined before packing and placement in a sterilizer. After sterilization, instruments are stored until needed in the Operating Room.

The time between sterilization and use may range from a few minutes to several weeks, thus the packaging materials and methods must allow for penetration of sterilant (i.e. saturated steam) during the sterilization process as well as protect the instruments from contamination during storage and handling. If the physical, microbial barrier provided by the sterilization packaging is compromised, the set of instruments is considered contaminated and must be reprocessed before use. Having to reprocess an instrument set can have undesired consequences, including decreased productivity in the CS Department and delayed surgeries. In an emergency situation, hospitals may use flash sterilization, a process which, though designed for the steam sterilization of patient care items for immediate use, may put patients at risk for increased surgical-site infections. Thus, reprocessing instruments is considered to be a major problem for Operating Rooms and CS Departments alike.

"Wet packs" are one reason packaged instrument sets may be deemed non-sterile and require reprocessing. An instrument set is considered wet when moisture in the form of dampness, droplets, or puddles of water is observed on or within a sterilization package such as a rigid container, non-woven wrap, peel pouch, or instrument after a completed steam sterilization cycle. Very simply, moisture can act as a vehicle to carry microorganisms inside the pack and contaminate the sterile instruments; making wet packs a significant problem in sterility assurance.

There are several potential causes for wet packs, including improper preparation/configuration of instrument sets, incorrect packaging materials or methods, improper loading of the sterilizer, insufficient drying time, improper cooling methods, poor steam quality, improperly drained steam supply lines, and/or improper cycle selection. Moisture on the outside of packs can usually be detected as soon as the packaged instruments are removed from the sterilizer. Internal pack moisture, however, can remain undetected until the packaged instrument sets are opened at the point of use. It is in this instance where latent internal moisture is discovered at the point of use in the Operating Room, where time and sterility assurance are most critical, that wet packs present the biggest problem.

Although the use of moisture indicators, such as colorimetric moisture indicating media, as wet pack indicators is possible, implementation is not straightforward. One possible method of using the indicating media is to place the media inside a test pack—a model package constructed to simulate the penetration and evacuation of steam in an instrument sterilization package. Unfortunately, a steam sterilization load often contains a mixture of different types of sterilization packaging (e.g., wrapped instrument sets, rigid containers, etc.) and different amounts of materials contained within the packaging, thereby limiting the use and construction of a universal test pack. Additionally, varying the number of packages in a load can also affect the outcome of wet pack generation for certain types of packages. The use of multiple test packs designed to simulate a wider range of packaging types and loading conditions may be possible, however, the additional test packs may take up valuable space within the sterilizer as well as add considerable complexity for the operator in determining which test packs to use for the various combinations of packaging and load levels. The latter concern may lead to increased operator error.

Alternatively, the indicating media may be placed directly into each sterilization package to indicate the level of moisture in each individual package environment. However, the typical sterilization package is usually non-transparent, complicating direct visual observation of the indicator. One option is to open the package to directly observe the indicator. However, opening compromises the sterility of the instruments inside the package, so this can only be done if the instruments are to be used immediately after opening. Another option is to introduce a transparent or sheer element within the container or wrap through which the indicator can be visualized. Although such modified packaging may be possible, the modification would add significant costs and complexity to sterilization packages.

SUMMARY

The present disclosure is directed towards articles and packages for indicating wet packs and wet pack conditions after steam sterilization. There is a need for a low-cost, simple, effective, and adaptable indicator for providing early indication of wet packs following steam sterilization.

The present disclosure generally provides post-steam sterilization wet pack indicators comprising a moisture-indicating layer disposed on or near a first surface of a moisture-impermeable layer. The area of the moisture-indicating layer is dimensionally smaller than the area of the moisture-impermeable layer such that the edges of the moisture-impermeable layer extend beyond the edges of the moisture-indicating layer. The moisture-indicating layer generally comprises a reversible colorimetric steam-sterilization compatible moisture-indicating medium.

In some embodiments, the moisture-impermeable layer has a recess, and the moisture-indicating layer is disposed within the recess.

The present disclosure also provides for moisture-indicating articles comprising a moisture-permeable material, a moisture-impermeable layer peripherally bonded to the moisture-permeable material, and a moisture-indicating layer disposed between the moisture-permeable material and the moisture-impermeable layer. The moisture-indicating layer generally comprises a reversible colorimetric steam-sterilization compatible moisture-indicating medium.

The present disclosure also provides for a package comprising an enclosure defining a cavity and surgical instruments situated within the cavity. Generally, at least a portion of the enclosure comprises a moisture-permeable material, and a wet pack indicator is disposed upon a surface of the moisture-permeable material. The indicator generally comprises a moisture-impermeable barrier layer and a moisture-indicating layer comprising a reversible colorimetric steam-sterilization compatible moisture-indicating medium. The moisture-impermeable layer of the wet pack indicator is peripherally bonded to the moisture-permeable material such that the moisture-indicating layer is disposed between the moisture-permeable material and the moisture-impermeable layer.

The above summary is not intended to describe each disclosed embodiment of every implementation of the present invention. The details of one or more embodiments of the invention are also set forth in the description below. Other features, objects, and advantages of the invention will be apparent from the description and from the claims.

DETAILED DESCRIPTION

Figure 1A:
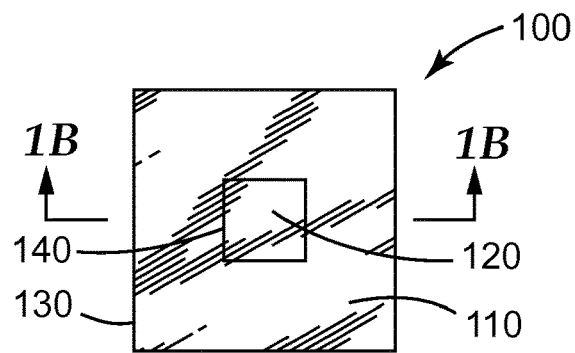
FIG. 1A is a top view perspective of a wet pack indicator according to certain embodiments of the present disclosure.

In the following description, reference is made to the accompanying set of drawings that form a part of the description hereof and in which are shown by way of illustration several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

As used herein:

"Bis(glyoxime)-transition metal complex" refers to a complex that has two glyoxime moieties complexed to a transition metal; as described further herein, the glyoxime moieties may have alkyl or other groups substituted for hydrogen at the ortho positions.

"Glyoxime" refers to vicinal dioximes of substituted or unsubstituted orthoketones.

"Humidity" and "moisture" are used interchangeably to include all forms of water, e.g. water vapor and liquid forms, present in an environment or adsorbed onto the surface of the moisture-indicating medium;

"Moisture-permeable," "moisture-penetrable," "steam-permeable," and "steam-penetrable" are used interchangeably herein;

"Visible spectroscopic reflection color intensity change" refers to the difference observed between two color states and in some embodiments can be expressed as difference in Hue.

"Visible spectroscopic reflection" refers to measurements of reflections that are typically in the near UV-visible region of the electromagnetic spectrum—from about 350 nm to about 830 nm; it is understood that the actual reflection spectrum of a particular composition may be influenced by solvent, solvation, interference of thin surface coatings, and other environmental parameters such as temperature.

"Optical spectrum" refers to the spectrum of reflected and/or transmitted electromagnetic radiation in the near visible and visible wavelengths from and/or through an object. In some cases, the change in optical spectrum is a visible color change.

"Transition metal" refers to any element or elements having atomic numbers from 21-30, 39-48, 72-80, and 104-112. Exemplary transition metals include zirconium, titanium, rhodium, iridium, platinum, palladium, gold, nickel, copper, and combinations thereof.

Unless otherwise specified, as used herein, all relative humidity values refer to relative humidity as measured at room temperature (between 22° C. and 28° C.).

A variety of products and articles, including, for example, medical instruments, devices, bandages, and equipment, must be sterilized prior to use to prevent bio-contamination of a wound site, a sample, an organism, or the like. Typically, the items used in medical procedures are placed into a container and wrapped with a flexible wrap (e.g., a cloth or sheet) made of a sterilant-permeable material or the items are placed into a reusable vented rigid container that allows permeation of the sterilant through the venting region. A number of sterilization processes are used that involve contacting the product or article with a sterilant. Examples of such sterilants include steam, ethylene oxide, hydrogen peroxide, and the like. Steam sterilization is widely used, at least in part because multiple batches of articles can be subjected to sterilization conditions during a 24 hour period using a single steam sterilizer. However, various conditions relating to the steam sterilization cycle or the packaging can result in the presence of moisture within the packs after sterilization, thereby compromising the sterility of the pack's contents. These so-called wet packs continue to be a problem in steam sterilization procedures.

There is a need in hospital CS Departments for a solution for providing a low-cost, simple, effective, and adaptable indicator for early indication of wet packs and wet pack conditions following steam sterilization. If identified early, wet packs may be reprocessed early so that only non-compromised sterile packs are transported to the Operating Room.

Some irreversible moisture indicators have been used to provide confirmation of the presence of steam during operation of steam sterilization autoclaves. However, once these moisture indicators have been subjected to the sterilization cycle, they are incapable of providing any information about the presence or absence of moisture, and thereby wet pack conditions, after sterilization and drying. Additionally, many of the irreversible indicators for testing the presence of steam during sterilization are present on the outside of sterilization packages, thus providing information only for the environment external to the sterilization packages. The internal environment of a sterilization package is usually the most reliable indication of wet pack conditions since the interior of the package is usually the most difficult, and the last environment to dry during the drying cycle following steam sterilization. Although reversible colorimetric moisture indicators can be placed inside sterilization packages and test packs to indicate the presence of moisture and wet pack conditions in the internal environment of a sterilization packages after steam sterilization, as described in U.S. Provisional Application No. 61/726,264 filed Nov. 14, 2012 and U.S. Provisional Application No. 61/792,168 filed on Mar. 15, 2013, both incorporated herein in their entirety, problems may arise with viewing and obtaining information from such indicators without compromising the sterilization integrity of a sterilization package by opening or unwrapping the package.

One method for viewing and obtaining information from moisture indicators and wet pack indicators regarding the interior environment of a sterilization package is to place the indicator inside a test pack, then open the test pack and inspect the indicator following steam sterilization and drying cycles. A test pack is generally a model package constructed to simulate the penetration and evacuation of steam in a sterilization package containing instruments. Since the test pack does not usually contain instruments that are to be used in medical procedures, the test pack can be placed in the same sterilization cycles as the instrument sterilization packages, and can be opened and examined following sterilization without compromising any instruments intended for medical procedures. Unfortunately, a steam sterilization load often contains a mixture of different types of sterilization packaging, such as wrapped instrument sets, rigid containers, and other sterilization package forms. Each sterilization package may also contain different amounts of materials within the packaging, thereby limiting the use and construction of a universal test pack. Additionally, varying the number of packages in a given sterilization load can also affect the outcome of wet pack generation for certain types of packages. The use of multiple test packs designed to simulate a wider range of packaging types and loading conditions may be possible, however, the additional test packs may take up valuable space within the sterilizer as well as add considerable complexity for the operator in determining which test packs to use for the various combinations of packaging and load levels. The latter concern may lead to increased operator error.

Another method for viewing and obtaining information from moisture indicators and wet pack indicators regarding the interior environment of a sterilization package is to place the indicator inside each sterilization package with the instruments. However, the typical sterilization package is usually non-transparent, complicating direct visual observation of the indicator. One option is to open the package to directly observe the indicator. However, opening compromises the sterility of the instruments inside the package, so this can only be done if the instruments are to be used immediately after opening. Another option is to introduce a transparent or sheer element, such as a window, within the container or wrap through which the indicator can be visualized. Although such modified packaging may be possible, the modification would add significant costs and complexity to sterilization packages.

It has been discovered that wet pack indicators that provide information about the interior sterilization package environment can be constructed for placement on the exterior of the sterilization package, thus allowing indication of wet packs and wet pack conditions without compromising the sterility of the package contents, adding the complexity and cost of introducing a sheer or transparent element to the packages, or requiring the complexity of test pack usage. The wet pack indicators described herein are reliable, simple, cost-efficient, and usable on different types of sterilization packages. The wet pack indicators described herein can withstand the temperatures and pressure of steam sterilization, have a highly visible color across a wide range of humidity levels, and can change qualitatively and/or quantitatively with a change in humidity to provide reliable indication of the amount of moisture present inside sterilized packs following steam sterilization, and can therefore provide reliable early indication of wet packs.

The present disclosure generally provides post-steam sterilization wet pack indicators. In some embodiments, the indicators comprise a moisture-indicating layer disposed on or near a first surface of a moisture-impermeable layer. Thus the invention can include both embodiments wherein the moisture-indicating layer is disposed directly upon the moisture-impermeable layer, and embodiments wherein there are one or more optional layers disposed between the moisture-impermeable layer and the moisture-indicating layer. The area of the moisture-indicating layer is dimensionally smaller than the area of the moisture-impermeable layer such that the edges of the moisture-impermeable layer extend beyond the edges of the moisture-indicating layer. The moisture-indicating layer generally comprises a reversible colorimetric steam-sterilization compatible moisture-indicating medium. In some embodiments, the moisture-impermeable layer has a recess, and the moisture-indicating layer is disposed within the recess. By moisture-impermeable, it is meant that the moisture-impermeable layer is substantially moisture impermeable such that the majority of moisture reaching the moisture-indicating layer does not pass through or across the moisture-impermeable layer.

The present disclosure also provides for moisture-indicating articles comprising a moisture-permeable material, a moisture-impermeable layer peripherally bonded to the moisture-permeable material, and a moisture-indicating layer disposed between the moisture-permeable material and the moisture-impermeable layer. The moisture-indicating layer generally comprises a reversible colorimetric steam-sterilization compatible moisture-indicating medium.

The present disclosure also provides for a package comprising an enclosure defining a cavity and surgical instruments situated within the cavity. Generally, at least a portion of the enclosure comprises a moisture-permeable material, and a wet pack indicator is disposed upon a surface of the moisture-permeable material. The indicator generally comprises a moisture-impermeable barrier layer and a moisture-indicating layer comprising a reversible colorimetric steam-sterilization compatible moisture-indicating medium. The moisture-impermeable layer of the wet pack indicator is peripherally bonded to the moisture-permeable material such that the moisture-indicating layer is disposed between the moisture-permeable material and the moisture-impermeable layer.

FIG. 1A depicts a top view perspective of one embodiment of a wet pack indicator 100 of the present disclosure. The wet pack indicator 100 comprises a moisture-impermeable layer 110 having a first surface, and a moisture-indicating layer 120 disposed upon the first surface of the moisture-impermeable layer 110. The area of the moisture-indicating layer 120 is dimensionally smaller than the area of the moisture-impermeable layer 110 such that the edges 130 of the moisture-impermeable layer extend beyond the edges 140 of the moisture-indicating layer. In some embodiments, the moisture-impermeable layer 110 may be transparent or sheer such that the color of the moisture-indicating layer 120 is visible through the moisture-impermeable layer 110. In some embodiments, the moisture-impermeable layer 110 may be non-transparent, opaque, or solid-colored such that the color of the moisture-indicating layer 120 is not visible through the moisture-impermeable layer 110. Where the moisture-impermeable layer is non-transparent, opaque, or solid-colored, the moisture-indicating layer of the wet pack indicator may be visually observed from the bottom side of the wet pack indicator (for example, after peeling the indicator off of a sterilization package).

Figure 1B:
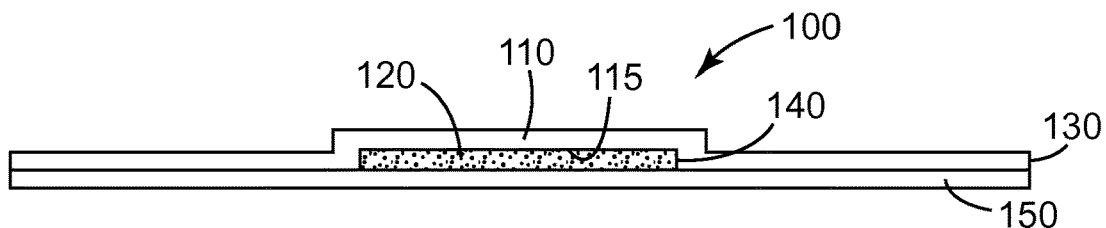
FIG. 1B is a cross-sectional view of a wet pack indicator according to certain embodiments of the present disclosure.

FIG. 1B depicts a cross-sectional view of a wet pack indicator 100 according to certain embodiments of the present disclosure. The wet pack indicator 100 comprises a moisture-impermeable layer 110 having a first surface 115, and a moisture-indicating layer 120 disposed upon the first surface 115 of the moisture-impermeable layer 110. The area of the moisture-indicating layer 120 is dimensionally smaller than the area of the moisture-impermeable layer 110 such that the edges 130 of the moisture-impermeable layer extend beyond the edges 140 of the moisture-indicating layer. The indicator may optionally include at least one base layer 150 comprising a release liner or other suitable material such as non-wovens, wovens, color-enhancing layers, adhesives, challenge layers, and wicking layers. In some embodiments, the moisture-impermeable layer 110 is peripherally bonded to the base layer 150 such that the moisture indicating layer 120 is disposed between the base layer 150 and the moisture-impermeable layer 110.

Figure 2:
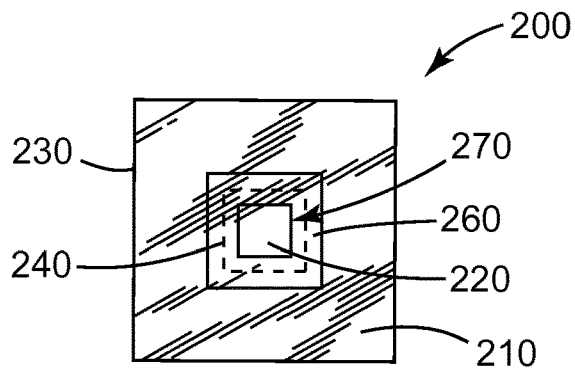
FIG. 2 is a top view perspective of a wet pack indicator according to certain embodiments of the present disclosure.

FIG. 2 depicts a top view perspective of one embodiment of a wet pack indicator 200 of the present disclosure. The wet pack indicator 200 comprises a moisture-impermeable layer 210 having a first surface, and a moisture-indicating layer 220 disposed upon the first surface of the moisture-impermeable layer 210. The area of the moisture-indicating layer 220 is dimensionally smaller than the area of the moisture-impermeable layer 210 such that the edges 230 of the moisture-impermeable layer extend beyond the edges 240 of the moisture-indicating layer.

In some embodiments, an optional color-enhancing layer 260 may be disposed between the moisture-impermeable layer 210 and the moisture-indicating layer 220. In some embodiments, the color-enhancing layer 260 may be disposed on the surface of the moisture-impermeable layer 210 opposite the first surface of the moisture-indicating layer 220. In some embodiments, the color of the moisture-indicating layer 220 can be visible through a viewing area 270. In some embodiments, the viewing area 270 is an open hole in the color-enhancing layer 260. In some embodiments, the viewing area 270 is a transparent or sheer material that is part of the color-enhancing layer 260. In some embodiments, the optional color-enhancing layer 260 is a solid, transparent or sheer layer that does not require a viewing area 270.

Figure 3:
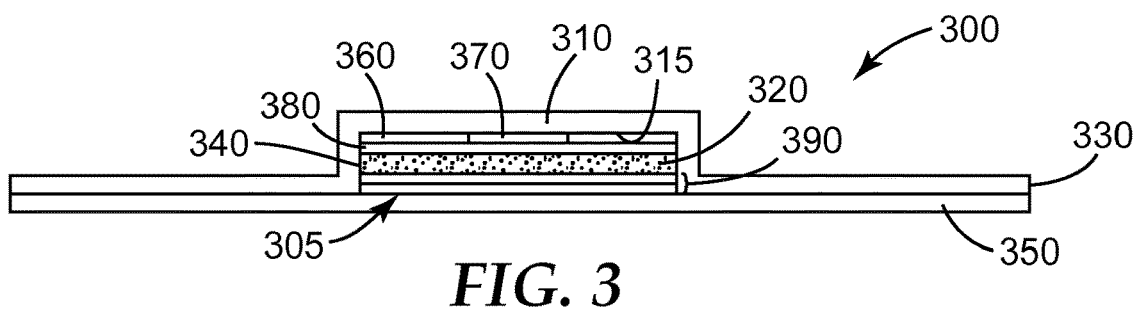
FIG. 3 is a cross-sectional view of a wet pack indicator according to certain embodiments of the present disclosure.

FIG. 3 depicts a cross-sectional view of a wet pack indicator 300 according to certain embodiments of the present disclosure. The wet pack indicator 300 comprises a moisture-impermeable layer 310 having a first surface 315, and a moisture-indicating layer 320 disposed on or near the first surface 315 of the moisture-impermeable layer 310. Where optional layers 360 and 380 are disposed between the moisture-impermeable layer 310 and the moisture-indicating layer 320, the moisture-indicating layer 320 is disposed near the first surface 315 of the moisture-impermeable layer 310. The area of the moisture-indicating layer 320 is dimensionally smaller than the area of the moisture-impermeable layer 310 such that the edges 330 of the moisture-impermeable layer extend beyond the edges 340 of the moisture-indicating layer. The indicator may optionally include a color-enhancing layer 360 and a viewing area 370 for viewing the moisture-indicating layer 320 through the color-enhancing layer 360. In some embodiments, the color-enhancing layer 360 may be disposed between the moisture-impermeable layer 310 and the moisture-indicating layer 320. In some embodiments, the color-enhancing layer may be disposed upon the moisture-impermeable layer 310 on the surface opposite the moisture-indicating layer 320. The indicator may include one or more optional middle layers 380 disposed between the moisture-indicating layer 320 and the moisture-impermeable layer 310. The optional middle layers may comprise color-enhancing layers, wicking layers and adhesives. Additional optional lower layers 390 may be disposed upon the surface of the moisture-indicating layer 320 opposite the moisture-impermeable layer 310. These optional lower layers 390 may comprise color-enhancing layers, adhesives, challenge layers, and wicking layers. In some embodiments, the moisture-impermeable layer 310 is peripherally bonded to one or more optional base layers 350 such that the moisture indicating layer 320 is disposed between the base layer(s) 350 and the moisture-impermeable layer 310. Suitable optional base layers 350 may include release liners, non-wovens, wovens, color-enhancing layers, adhesives, challenge layers, and wicking layers.

The optional color-enhancing layers 260, 360, middle layers 380, and lower layers 390 may have the same area size as the moisture-indicating layer 320, or may be bigger or smaller in dimensional area than the moisture-indicating layer 320. For example, in FIG. 2, the edges of the color enhancing layer 260 extend beyond the edges 240 of the moisture-indicating layer 220. Alternatively, in FIG. 3, the edges of all of the optional color-enhancing layers 360, middle layers 380, moisture-indicating layer 320, and lower layers 390 are coincident, thus resulting in the same dimensional area coverage for each layer (in this embodiment, the dimensional area of the viewing area 370 is included in the calculation of the dimensional area of the color-enhancing layer 360. In some embodiments, the area of the optional middle layers 380 and lower layers 390 is dimensionally smaller than the moisture-impermeable layer 310, and the edges 330 of the moisture-impermeable layer extend beyond the edges of the optional middle layers 380 and lower layers 390. The optional base layers 350 may have the same area size as the moisture-indicating layer 320 or the moisture-impermeable layer 310, or may be bigger or smaller in dimensional area than the moisture-indicating layer 320 or the moisture-impermeable layer 310.

In some embodiments, the moisture-impermeable layer 310 has a recess 305, and the moisture-indicating layer 320 and optional additional layers, such as one or more color-enhancing layers 360, one or more middle layers 380, and one or more lower layers 390 are disposed within the recess 305.

In some embodiments, the moisture-impermeable layer 110, 210, 310 can be formed by injection molding or by extruding suitable materials. Suitable materials that can be manufactured for use in the moisture-impermeable layer 110, 210, 310 include polycarbonate, polypropylene, polyamides, and various polyesters. Other suitable materials include silicon-based films, fluoropolymer-based films, and metal foils such as aluminum foil. In some embodiments, the moisture-impermeable layer may be in the form of a film and/or a tape.

The moisture-indicating layer 120, 220, 320 comprises a moisture-indicating medium and can exist in different structural forms. In some embodiments, the moisture-indicating layer can be in articulated bulk shape, monolith, or particulate forms, such as beads, pellets, spheres, granules, and extrudates. In some embodiments, the moisture-indicating layer can be in film form, such as coatings and free-standing films. In some embodiments, the moisture-indicating layer can be comprised of moisture-indicating media in the form of fibers, such as yarn, rods, and needles. In some embodiments, including where the moisture-indicating layer is disposed within a recess of the moisture-impermeable layer the moisture-indicating layer can comprise a free form, such as free-flowing particulates (e.g. powder, beads, granules).

Alternatively, the moisture-indicating layer 120, 220, 320 may comprise a multimedia construction of moisture-indicating media in combination with other media and/or containment devices. Exemplary multimedia constructions can include moisture-indicating media physically entangled in a fibrous web (e.g. particle-loaded webs), multilayer constructions (e.g., indicator particles or fibers sandwiched between containment layers), partially embedded or encapsulated constructions (e.g., particles or fibers partially embedded in a polymer, such as an adhesive-coated film or fiber; composites, such as an articulated bulk shape, film, or fiber). In some embodiments, the moisture-indicating medium may be adsorbed and/or impregnated on a solid (e.g., $CoCl_2$ supported on $SiO_2$, indicator dyes adsorbed onto paper).

In some embodiments, the moisture-indicating layer 120, 220, 320 can be comprised of moisture-indicating media deposited on backing material or carrier material according to conventional methods known in the art (e.g. moisture-indicating cards and tapes). Exemplary backing materials and carrier materials include those made of paper, polyethylene, polypropylene, polyester or composites of any of these materials.

The moisture-indicating layer 120, 220, 320 is generally dimensionally smaller in area than the moisture-impermeable layer 110, 210, 310 such that when the moisture-indicating layer 120, 220, 320 is disposed on or near the first surface of the moisture-impermeable layer 110, 210, 310, the edges 130, 230, 330 of the moisture-impermeable layer 110, 210, 310 extend beyond the edges 140, 240, 340 of the moisture-indicating layer 120, 220, 320. In some embodiments, the moisture-impermeable layer 110, 210, 310 is peripherally bonded to a base layer 150, 350 e.g. a nonwoven, such that the moisture-indicating layer 120, 220, 320 is disposed between the moisture-impermeable layer 110, 210, 310 and the base layer 150, 350. By peripherally bonded it is meant that the edges 130, 230, 330 of the moisture-impermeable layer 110, 210, 310 are completely bonded to the base layer such that the moisture-indicating layer 120, 220, 320 is completely enclosed between the moisture-impermeable layer 110, 210, 310 and the base layer 150, 350. It is intended that where the base layer 150, 350 is moisture-penetrable, moisture reaches the moisture-indicating layer 120, 220, 320 predominantly through the moisture-penetrable base layer 150, 350 rather than through other paths.

In some embodiments the moisture-indicating layer 120, 220, 320 is directly attached to the moisture-impermeable layer 110, 210, 310. In some embodiments, one or more optional middle layers 380 disposed between the moisture-indicating layer 120, 220, 320 and the moisture-impermeable layer 110, 210, 310 may comprise pressure-sensitive adhesive or heat-bondable adhesive to allow attachment of the moisture-indicating layer 120, 220, 320 to the moisture-impermeable layer 110, 210, 310. In some embodiments, the moisture-indicating layer 120, 220, 320 is extruded directly onto the moisture-impermeable layer 110, 210, 310. In some embodiments, the moisture-indicating layer 120, 220, 320 and the moisture-impermeable layer 110, 210, 310 are co-extruded.

The moisture-indicating layer 120, 220, 320 generally comprises reversible, colorimetric moisture-indicating media. The moisture-indicating media may be a compound or a composition. While any suitable steam-sterilization-compatible moisture-indicating medium can be used, some exemplary moisture-indicating media include bis(glyoxime) transition metal complexes bound to solid supports, as well as cobalt and copper salts, and pH indicator dyes. The moisture-indicating media may also be present in the form of molecular species, such as metal complexes. By steam-sterilization-compatible, it is meant that the moisture-indicating media can be subjected to steam sterilization without significantly altering or damaging the moisture-indicating properties of the moisture-indicating media.

In some embodiments, the color, reflection spectrum, or transmission spectrum of the moisture-indicating media is quantitatively related to the level of moisture in the environment in which the moisture-indicating media is located. In some embodiments, the moisture-indicating media quantitatively changes color, reflection spectrum, or transmission spectrum at relative humidities ranging from about 0% to about 90% relative humidity. In some embodiments, the moisture-indicating media quantitatively changes color, reflection spectrum, or transmission spectrum at relative humidities ranging from about 30% to about 80% relative humidity. In some embodiments, the moisture-indicating media quantitatively changes color, reflection spectrum, or transmission spectrum at relative humidities of about 10% to about 90%.

In some embodiments, the moisture-indicating medium can comprise cobalt and copper salts. In some embodiments, the salts will exhibit a visible color change when exposed to specific levels of moisture in the surrounding environment. The salts may alternately exhibit measurable changes in opacity, Hue, or reflection spectrum at when exposed to specific levels of moisture in the surrounding environment. Exemplary salts that can be used as the moisture-indicating medium in the methods, articles, and packages described herein include $CoCl_2$, $CoBr_2$, $Co(SCN)_2$, $CubCl_2$, $CuBr_2$, and combinations thereof. In one exemplary embodiment, the moisture-indicating medium comprises $CoCl_2$.

In some embodiments, the moisture-indicating medium can comprise pH-indicator dyes. Without wishing to be bound by theory, it is believed that pH-indicator dyes operate as moisture indicators because water from the surrounding environment (e.g., liquid water, condensation, water vapor, humidity, or relative humidity, etc.) can dilute the pH indicator compositions, causing the pH of these compositions to approach neutrality. As pH-indicator compositions dry, the environment around the pH indicator becomes acidic or basic, based on the particular composition, thus causing the pH-indicator dye in the composition to change color to indicate the change in pH. For example, phenolphthalein-based pH-indicator compositions may turn from pink to colorless as the pH-indicating composition dries from neutral (dilution) to basic state (dry), thus reflecting the level of moisture in the environment surrounding the pH-indicator composition. pH indicator dyes known in the art are useful as the moisture-indicating medium in the methods, articles, and packages described herein. Some exemplary pH-indicating dyes useful as the moisture-indicating medium in the methods, articles, and packages described herein include litmus, cyandin, neutral red, alizarin, alkali blue, thymolphthalein, phenolphthalein, crystal violet, chlorophenol red, cresol red, thymol blue, m-cresol purple, and p-xylenol blue.

In some embodiments, the moisture-indicating medium can comprise a solid support and a bis(glyoxime)-transition metal complex bound to the support. Compositions that include a solid support and a bis(glyoxime)-transition metal complex bound to the support can be used for colorimetric moisture or humidity determination. Depending upon composition, moisture-indicating media can be constructed which can quantitatively and reversibly determine the humidity level of the atmosphere to which the sensor is exposed.

In some embodiments, the solid support can include solid inorganic non-metal-oxide supports. Inorganic non-metal-oxide supports include inorganic solids having a polyatomic, oxygen-containing anion as identified in its crystal structure. In some embodiments, the inorganic non-metal-oxide supports are insoluble or only slightly soluble in water. In some embodiments, the inorganic non-metal-oxide supports have a solubility product (Ksp) value no greater than 1×10−3. Exemplary solid inorganic non-metal-oxide supports include phosphate, carbonate, sulfate, and hydroxide supports. In some embodiments, the non-metal-oxide inorganic support can include anhydrous calcium sulfate, zinc carbonate hydroxide, or calcium phosphate.

In some embodiments, the solid support can include organic polymeric supports. In general, hydrophilic polymers that have the ability to bind transition metal ions and their bis(glyoxime) complexes may be used. In some embodiments, ion exchange polymers having exchangeable ions bound to the polymer may be used. Herein, ion exchange generally refers to the exchange of ions attached to the polymer with the transition metal ions of the bis (glyoxime) transition metal complexes described herein. In some embodiments, solid organic polymeric supports may include polymers with functional groups capable of binding transition metal ions such as sulfonates, phosphates, and carboxylates. Suitable organic polymers may be natural or synthetic. Some exemplary organic polymeric supports include polyamides, polycarbonates, polyalkylene glycols, polyvinyl alcohols, polyvinyl ethers, alkyl cellulose, hydroxyalkyl celluloses, cellulose ethers, cellulose esters, nitro celluloses, methyl cellulose, ethyl cellulose, hydroxy-propyl cellulose, hydroxy-propyl methyl cellulose, hydroxy-butyl methyl cellulose, cellulose acetate, cellulose propionate, cellulose acetate butyrate, cellulose acetate phthalate, carboxylethyl cellulose, cellulose triacetate, and cellulose sulphate sodium salt.

In some embodiments, the solid organic polymeric support is a strong acid cation exchange resin. As used herein, the term "strong acid" refers to an acidic group that dissociates completely in water. Strong acids typically have a pKa less than 4 or 5. The strong acid cation exchange resins typically have ionic groups such as sulfonic acid groups (—SO3H), phosphonic acid groups (—PO3H2), or salts thereof. When present as a salt, the sulfonic acid groups are present as sulfonate anions and the phosphonic acid groups are present as phosphonate anions. Suitable salts often have cations selected from an alkali metal ion (e.g., sodium ion, lithium ion, or potassium ion), an alkaline earth metal ion (e.g., calcium or magnesium), an ammonium ion, or an ammonium ion substituted with one or more alkyl groups, aryl groups, or combinations thereof.

The cation exchange resins are typically crosslinked polymeric materials prepared from various ethylenically unsaturated monomers. The polymeric materials are usually based mainly on styrene, derivatives of styrene (e.g., alpha-methyl styrene), (meth)acrylates, or combinations thereof. The polymeric materials are typically crosslinked to provide the needed amount of rigidity. The cation exchange resins can be in the form of beads, films, fibers, or any other desired form.

In some embodiments, the cation exchange resins are polymeric materials prepared from styrene or derivatives of styrene. Divinyl benzene is commonly used as a crosslinker. The acidic groups can be introduced during the polymerization process by the inclusion of a monomer having an acidic group. Suitable monomers with an acidic group include, for example, 4-stryrene sulfonic acid, vinylsulfonic acid, or a salt thereof in the monomer mixture. Alternatively, the acidic group can be introduced after the polymerization process by treating the polymeric material with a sulfonating agent.

In other embodiments, the cation exchange resins are based on polymeric materials prepared from (meth)acrylate monomers. Monomers with multiple (meth)acryloyl groups can be used as a crosslinker. The acidic group can be introduced during the polymerization process by the inclusion of a monomer having a sulfonic acid group (e.g., N-acrylamidomethanesulfonic acid, 2-acrylamidoethanesulfonic acid, 2-acrylamido-2-methylpropanesulfonic acid, and 2-methacrylamido-2-methylpropanesulfonic acid, or a salt thereof) or by inclusion of a monomer having a phosphonic acid group (e.g., 2-acrylamidoethylphosphonic acid and 3-methacrylamidopropylphosphonic acid, or a salt thereof) Suitable (meth)acrylate-based strong cation exchange resins are further described in U.S. Pat. No. 7,098,253 (Rasmussen et al.), U.S. Pat. No. 7,683,100 (Rasmussen et al.), and U.S. Pat. No. 7,674,835 (Rasmussen et al.).

Strong acid cation exchange resins are commercially available from multiple suppliers. Examples include the cation exchange resins commercially available from Dow Chemical (Midland, Mich.) under the trade designation AMBERLYST (e.g., AMBERLYST 15, AMBERLYST 35, AMBERLYST 40, and AMBERLYST 70), under the trade designation DOWEX (e.g., DOWEX MARATHON and DOWEX MONOSPHERE), under the trade designation AMBERJET (e.g., AMBERJET 1000H), and under the trade designation AMBERLITE (e.g., AMBERLITE IR120H).

The strong acid cation exchange resin can be a gel-type resin or macroporous (i.e., macroreticular) resin. As used herein, the term "macroporous" refers to particles that have a permanent porous structure even in the dry state. Although the resins can swell when contacted with a solvent, swelling is not needed to allow access to the interior of the particles through the porous structure. In contrast, gel-type resins do not have a permanent porous structure in the dry state but must be swollen by a suitable solvent to allow access to the interior of the particles. In many embodiments, the strong acid cation exchange resins are macroporous. Macroporous resins tend to have a higher crosslinking density compared to gel-type resins.

The ion exchange capacity of the cation exchange resins if often at least 0.2 equivalents per liter, at least 0.5 equivalent per liter, at least 1 equivalents per liter, or at least 2 equivalents per liter. The capacity is often up to 10 equivalents per liter, up to 8 equivalents per liter, or up to 5 equivalents per liter. The capacity can be, for example, in a range of 0.1 to 10 equivalents per liter, in a range of 0.5 to 10 equivalents per liter, or in a range of 0.5 to 5 equivalents per liter. High capacity is often desired to adsorb more of the transition metal ion that is part of the bis(glyoxime)-transition metal complex onto the cation exchange resin.

In some embodiments, the solid support can include solid metal oxide supports. The solid metal oxide supports can be relatively colorless (e.g. clear, white, etc.) and capable of adsorbing or bonding to chromophoric species. In some embodiments, the provided solid metal oxide supports include oxides of silicon, aluminum, zirconium, titanium, or combinations thereof. Non-limiting examples of suitable metal oxides include silicon oxide, aluminum oxide, tin oxide, zinc oxide, titanium oxide, zirconium oxide, lanthanide ("rare-earth") oxides, and mixtures thereof. Metal oxide supports can also include inorganic polymers (geopolymers) formed by reaction of a reactive solid aluminosilicate source such as a dehydroxylated clay with alkali silicate solution, such as those described in MacKenzie et al., Materials Letters, 63, 230-232 (2009). In some embodiments, the provided solid metal oxide supports can include alumina or silica gels, beads, or solid supports. Other exemplary metal oxide supports include zirconium oxide pellets and titanium (IV) oxide pellets. In some embodiments the solid metal oxide supports may comprise beads, pellets, spheres, granules, extrudates, tablets, nanoparticles, fibers, rods, needles, wovens, or non-wovens. In some embodiments, the metal oxide support may be in film form, such as coatings and free-standing films.

In some embodiments, the moisture-indicating media comprises a bis(glyoxime)-transition metal complex bound to the solid support. By bound it is meant that there is an attractive interaction between the bis(glyoxime)-transition metal complex and the solid support. The attractive interaction can include covalent bonds, ionic bonds, dative bonds, metallic bonds, hydrogen bonds, van der Waals forces, electrostatic forces, chemisorption, physisorption, or any other interaction that attracts the bis(glyoxime)-transition metal complex to the solid support. For example, when a bis(glyoxime)-transition metal complex that is insoluble in water or slightly soluble in water is bound to a solid support, it is typically not removed by successive or continuous rinsing with water. In some embodiments, the attractive interaction includes hydrogen bonds.

The bis(glyoxime)-transition metal complex includes two glyoxime moieties that form a complex with transition metals. The bis(glyoxime)-transition metal complex generally has the structure of Formula (I):

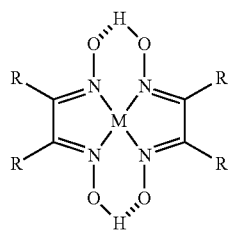

(I)

wherein:

M is a transition metal; and

R is independently selected from the groups comprising alkyl, such as ethyl and methyl; aryl, such as phenyl; thioaryl, such as thiophenyl; and a heterocyclic group, such as piperidine and morpholine.

Common glyoxime moieties include dialkylglyoximes such as, for example, dimethylglyoxime and diethylglyoxime. Common glyoximes that may also be useful in the provided compositions include diphenylglyoxime and bis(thiophenyl)glyoxime. Additionally, morpholine and piperidine have been reacted with anti-chloroglyoxime to give morpholineglyoxime and piperidineglyoxime. Since the transition metal ion complexes with the heteroatoms of the glyoxime species (nitrogen and oxygen, for example) it is contemplated that other substituents on the glyoxime molecule may be useful compositions if they do not interfere with the ability of the two glyoxime moieties to complex with a transition metal ion. When complexed, the bis(glyoxime)-transition metal complex typically has a square planar configuration. In some embodiments, the bis(glyoxime)-transition metal complex can include ions of rhodium, iridium, platinum, palladium, gold, nickel or copper which are well known by those of ordinary skill in the art to form square planar coordination complexes with glyoxime moieties like dimethylglyoxime. An exemplary bis(glyoxime)-transition metal complex for use in the moisture-indicating media is nickel dimethylglyoxime. A structure of an exemplary nickel bis(dimethylglyoxime) complex, bis-(dimethylglyoximato) nickel (II), is shown in Formula (II) below:

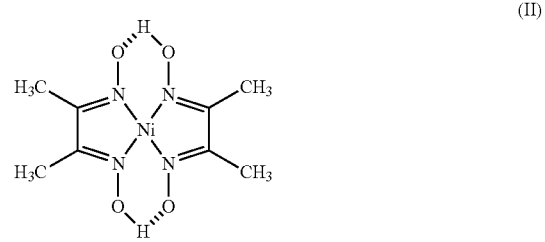

(II)

Using some of the above-identified compositions, colorimetric moisture-indicating media can be constructed. For example, when the solid metal oxide support is aluminum oxide, silicon oxide, or a combination thereof, and when the bis(glyoxime)-transition metal complex includes nickel and two dimethylglyoxime moieties (the complex shown in Formula (II)) a reversible colorimetric moisture-indicating media can be formed.

The color of the embodied moisture-indicating media can change quantitatively and reversibly according to the amount of moisture (e.g., liquid water, condensation, humidity, or relative humidity, etc.) in contact with the moisture-indicating layer 120, 220. For example, a provided composition that includes bis(glyoxime)-transition metal complex (bis-(dimethylglyoximato)-nickel (II)) has a strong absorption at wavelengths from about 460 nm to about 570 nm with a peak at a wavelength of around 520 nm. The visible spectroscopic reflection intensity in the wavelength range of 460 nm to 560 nm and color of the composition changes quantitatively and reversibly according to the amount of moisture (e.g., liquid water, condensation, humidity, or relative humidity, etc.) in contact with the composition. By quantitatively it is meant that the reflection intensity in the wavelength range of 460 nm to 560 nm and therefore the color has a one-to-one correlation to the amount of humidity. By reversible it is meant that when the composition is exposed to one set of humidity conditions it has a specific absorption; when the set of humidity conditions is changed, the composition changes color to give a different specific reflection spectrum; and, when the composition is returned to the initial set of humidity conditions, the spectroscopic reflection spectrum (or color) returns to the original specific absorption. The visible absorbance peaks or reflection valleys of many other bis(glyoxime)-transition metal complexes having a square planar configuration are well known.

In some embodiments, the moisture-indicating medium can comprise a solid metal oxide support, a bis(glyoxime)-transition metal complex bound to the support, and a silyl-containing compound bound to the solid metal oxide support through a silanol bond with at least one hydroxyl group on the surface of the solid metal oxide support. In some embodiments, no more than about 50% of surface hydroxyl groups of the support are bound to the silyl-containing compound. The bis(glyoxime)-transition metal complex and the solid metal oxide support are described above.

Silyl-containing compounds having hydroxyl or hydrolyzable groups can react with surface hydroxyl groups of metal oxides and displace the hydroxyl or hydrolyzable groups on the silyl-containing compound to form a covalent —Si—O—M— bond (M is a metal or Si). Through this silanization, the surface of metal oxides can be covered by the silyl-containing groups. The properties of the modified metal oxide surfaces at least partially reflect the characteristics of the silyl-containing groups.

The silane modification of the solid metal oxide support can be accomplished in a variety of known ways. In some embodiments, the solid metal oxide support can be contacted with the silyl-containing compound to form a silane-modified solid metal oxide support. In some embodiments, no more than about 50% of surface hydroxyl groups of the metal oxide support are bound to the silyl-containing compound. In some embodiments, no more than 40%, 30%, 20%, or 10% of surface hydroxyl groups of the metal oxide support are bound to the silyl-containing compound.

In some embodiments, the solid metal oxide support is mixed into or contacted with a modification composition comprising a silyl-containing compound and an acid. The silyl-containing compound is generally present in the modification composition in amounts ranging from about 0.01% to about 10% (e.g., between 0.1% and 10%, between 0.5% and 5%, or between 1% and 3%) by weight, based on the total weight of the modification composition. The acid may be an organic or inorganic acid. Exemplary organic acids include acetic acid, citric acid, and formic acid. Exemplary inorganic acids include sulfuric acid, hydrochloric acid, and phosphoric acid. The acid will generally be included in the modification composition in an amount between about 0.005 and 10% (e.g., between 0.01 and 10% or between 0.05 and 5%) by weight, based on the total weight of the modification composition. In some embodiments, the modification composition additionally includes water. In some embodiments, the amount of water is between 0.1% and 99.9% (e.g., 0.5% to 95%, 0.5% to 90%, etc.) by weight based on the total weight of the modification composition.

In some embodiments, the solid metal oxide support is mixed into or contacted with a modification composition comprising a silyl-containing compound and a solvent. The silyl-containing compound is generally present in the modification composition in amounts ranging from about 0.1% to about 10% (e.g., between 0.05% and 5% or between 1% and 3%) by weight of the modification composition. Generally, the solvent is organic. Exemplary solvents include toluene, alcohols (e.g., ethanol, isopropanol, etc.), tetrahydrofuran, and hydrocarbon solvents (e.g., hexane, etc.). The solvent will generally be included in the modification composition in an amount between about 0.5% and 99.9% (e.g., between 1% and 99.5%, between 90% and 99%, etc.) by weight, based on the total weight of the modification composition.

In some embodiments, the solid metal oxide support and the silyl-containing compound may be reacted in an oven at elevated temperatures. Oven temperatures can range from 50° C. to 150° C. (e.g., 50° C. to 90° C., 100° C. to 130° C., 110° C. to 120° C., etc.). Oven reaction times can range from 10 hours to 20 hours (e.g., 12 hours to 18 hours or 14 hours to 16 hours). In some embodiments, the solid metal oxide support and the silyl-containing compound may be reacted through vapor deposition.

Various silyl-containing compounds can be used to modify the solid metal oxide support. In some embodiments, the silyl-containing compound is of Formula (III):

$$R^1—Si(R^2)_{3-x}(R^3)_x \quad (III)$$

wherein $R^1$ is an alkyl, fluoroalkyl, alkyl substituted with an amino, aryl, aralkyl, or alkaryl group; each $R^2$ is independently hydroxyl or a hydrolyzable group; each $R^3$ is independently a non-hydrolyzable group; and x is an integer equal to 0, 1, or 2.

In some embodiments, the silyl-containing compound is of Formula (IV)

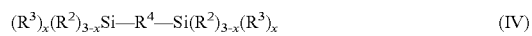

$$(R^3)_x(R^2)_{3-x}Si—R^4—Si(R^2)_{3-x}(R^3)_x \quad (IV)$$

wherein $R^4$ is an alkylene, arylene, or a combination thereof; each $R^2$ is independently hydroxyl or a hydrolyzable group; each $R^3$ is independently a non-hydrolyzable group; and x is an integer equal to 0, 1, or 2.

In some embodiments, the hydrolyzable group can include alkoxy, aryloxy, acyloxy, halo, —N($R^5$)$_2$, or —NH—Si($R^5$)$_3$ where $R^5$ is alkyl and the non-hydrolyzable group can include alkyl, aryl, aralkyl, or alkaryl. In some embodiments, the non-hydrolyzable group is alkyl, aryl, aralkyl, or alkaryl.

"Hydrolyzable group" refers to one of more groups bonded to a silicon atom in a silyl group that can react with water having a pH of 1 to 10 under conditions of atmospheric pressure. The hydrolyzable group is often converted to a hydroxyl group when it reacts. The hydroxyl group often undergoes further reactions such as reactions with hydroxyl groups on a surface of a metal oxide support. Exemplary hydrolyzable groups include, but are not limited to, alkoxy, acyloxy, halo, —N($R^5$)$_2$, or —NH—Si($R^5$)$_3$ where $R^5$ is alkyl.

"Non-hydrolyzable group" refers to one of more groups bonded to a silicon atom in a silyl group that can react with water having a pH of 1 to 10 under conditions of atmospheric pressure. These groups typically do not undergo reactions such as reactions with hydroxyl groups on a surface of a metal oxide support. Exemplary non-hydrolyzable groups include, but are not limited to alkyl, aryl, aralkyl, and alkaryl.

"Alkyl" refers to a monovalent group that is a radical of an alkane. The alkyl group can have 1 to 40 carbon atoms. The alkyl group can be linear, branched, cyclic, or a combination thereof. When the alkyl is linear, it can have 1 to 40 carbon atoms, 1 to 30 carbon atoms, 1 to 20 carbon atoms, or 1 to 10 carbon atoms. When the alkyl is branched or cyclic, it can have 3 to 40 carbon atoms, 3 to 30 carbon atoms, 3 to 20 carbon atoms, or 3 to 10 carbon atoms.

"Alkylene" refers to a divalent group that is a radical of an alkane. The alkylene group can have 1 to 40 carbon atoms. The alkylene group can be linear, branched, cyclic, or a combination thereof. When the alkylene is linear, it can have 1 to 40 carbon atoms, 1 to 30 carbon atoms, 1 to 20 carbon atoms, or 1 to 10 carbon atoms. When the alkylene is branched or cyclic, it can have 3 to 40 carbon atoms, 3 to 30 carbon atoms, 3 to 20 carbon atoms, or 3 to 10 carbon atoms.

"Aryl" refers to a monovalent group that is a radical of an aromatic carbocyclic compound. The aryl group has at least one aromatic carbocyclic ring and can have 1 to 5 optional rings that are connected to or fused to the aromatic carbocyclic ring. The additional rings can be aromatic, aliphatic, or a combination thereof. The aryl group usually has 5 to 20 carbon atoms. In some embodiments, the aryl group is phenyl.

"Arylene" refers to a divalent group that is a radical of an aromatic carbocyclic compound. The arylene group has at least one aromatic carbocyclic ring and can have 1 to 5 optional rings that are connected to or fused to the aromatic carbocyclic ring. The additional rings can be aromatic, aliphatic, or a combination thereof. The aryl group usually has 5 to 20 carbon atoms. In some embodiments, the arylene is phenylene.

"Alkoxy" refers to a monovalent group of formula —OR where R is an alkyl as defined above. In some embodiments, the alkoxy is methoxy, ethoxy, or propoxy.

"Fluoroalkyl" refers to an alkyl having at least one hydrogen atom replaced with a fluoro.

"Aryloxy" refers to a monovalent group of formula —OAr where Ar is an aryl group.

"Acyloxy" refers to a monovalent group of formula —O(CO)—Ra where Ra is an alkyl, aryl, aralkyl, or alkaryl. In some embodiments, the acyloxy is —O(CO)CH3 (acetoxy).

"Halo" refers to a monovalent group that is a radical of a halogen atom. The halo can be fluoro, chloro, bromo, or iodo. In some embodiments, the halo is chloro.

"Aralkyl" refers to an alkyl group substituted with at least one aryl group. The aralkyl group contains 6 to 40 carbon atoms. The aralkyl group often contains an alkyl group having 1 to 20 carbon atoms and an aryl group having 5 to 20 carbon atoms.

"Alkaryl" refers to an aryl group substituted with at least one alkyl group. The aralkyl group contains 6 to 40 carbon atoms. The aralkyl group often contains an aryl group having 5 to 20 carbon atoms and an alkyl group having 1 to 20 carbon atoms.

"Amino" refers to a monovalent group of formula —N($R^6$) where $R^6$ is hydrogen or alkyl.

The specific silyl-containing compound can be chosen based on the desired relative humidity at which the final moisture-indicating layer 120, 220 should undergo sharp color change. The characteristics of the silyl-containing compound (hydrophobic, hydrophilic, etc.) generally correlate to the relative humidity at which the final moisture-indicating composition shows significant color change. One silyl-containing compound or mixtures of two or more silyl-containing compounds can be used to modify the solid metal oxide support and adjust the color response of the moisture-indicating compositions. In some embodiments, the silyl-containing compound may be hydrophobic. For example, hydrophobic compounds of Formula (III), include compounds where group $R^1$ plus any non-hydrolyzable group $R^3$ are hydrophobic. As another example, hydrophobic compounds of Formula (IV), include compounds where group $R^4$ plus any non-hydrolyzable group $R^3$ are hydrophobic.

Exemplary silyl-containing compounds that may be bound to the solid metal oxide support in some embodiments of the moisture-indicating media include, but are not limited to, acetoxytrimethylsilane, t-butyldimethylchlorosilane, cyclohexylmethyldichlorosilane, cylcohexylmethyldimethoxysilane, 1,3-di-n-butyltetramethylsilazane, diethoxydimethylsilane, (diethylamino)trimethylsilane, (dimethylamino)trimethylsilane, diisopropyldichlorosilane, diisopropyldimethoxysilane, dimethyldichlorosilane, dimethyldiethoxysilane, dimethyldimethoxysilane, diphenyldichlorosilane, diphenyldiethoxysilane, diphenyldimethoxysilane, diphenylmethyldichlorosilane, dodecyltrichlorosilane, ethyltriacetoxysilane, ethyltrichlorosilane, ethyltrimethoxysilane, hexadecyltrimethoxysilane, hexanethyldisilazane, hexyltrimethoxysilane, isobutyltrimethoxysilane, isooctyltriethoxysilane, isooctyltrimethoxysilane, isobutyltriethoxysilane, methyltriacetoxysilane, methyltrichlorosilane, methyltriethoxysilane, methyltrimethoxysilane, n-octadecyldimethylchlorosilane, n-octadecyltrichlorosilane, n-octadecyltrimethoxysilane, n-octyltrichlorosilane, n-octyltriethoxysilane, n-octyltrimethoxysilane, phenethyltrimethoxysilane, phenyldimethylchlorosilane, phenylmethyldimethoxysilane, phenyltrichlorosilane, phenyldimethylchlorosilane, phenyltriethoxysilane, phenyltrimethoxysilane, n-propyltrichlorosilane, n-propyltriethoxysilane, n-propyltrimethoxysilane, trimethylchlorosilane, trimethyltriethoxysilane, trimethylmethoxysilane, 1H,1H,2H,2H-perfluoroctyldimethylchlorosilane, (3-aminopropyl)triethoxysilane, bis(triethyoxysilyl)ethane, and 1(triethoxysilyl)-2-(diethoxymethylsilyl)-ethane.

In some embodiments, the wet pack indicator includes one or more optional base layers 150, 350. Where more than one optional base layer 150, 350 is included, each layer may be constructed of the same material as or different material from the other optional base layers 150, 350. Suitable base layer 150, 350 materials include release liners, non-wovens, wovens, color-enhancing materials, challenge materials, wicking materials, adhesives, exterior walls of a sterilization package or container, polymeric matrices, and paper. In some embodiments, the wet pack indicator can include one or more optional middle layers 380 disposed between the moisture-impermeable layer 110, 210, 310 and the moisture-indicating layer 120, 220, 320. Such optional middle layers 380 can include adhesives, wicking layers, and color-enhancing layers. Where more than one optional middle layer 380 is included, each layer may be constructed of the same material as or a different material from the other optional middle layers 380. In some embodiments, the wet pack indicator can include one or more optional lower layers 390 disposed on the surface of the moisture-indicating layer 120, 220, 320 opposite the moisture-impermeable layer 110, 210, 310. In some embodiments, these optional layers 390 are disposed between the moisture-indicating layer 120, 220, 320 and the one or more optional base layers 150, 350. Such optional layers 390 can include adhesives, color-enhancing layers, challenge layers, and wicking layers. Where more than one optional layer 390 is included, each layer may be constructed of the same material as or a different material from the other optional layers 390.

Suitable release liner materials are known in the art. Exemplary release liner materials include fluorochemicals, silicones, and acrylic or urethane polymers.

Suitable adhesives may include pressure-sensitive adhesives, repositionable adhesives, heat-bondable adhesives, hot-melt adhesives, and other adhesives known in the art. Exemplary pressure-sensitive adhesives preferably include water-resistant pressure sensitive adhesive such as cross-linked acrylics, tackified rubber adhesives (e.g. natural rubber polyisoprene styrene butadiene rubber), and the like. Exemplary repositionable adhesives include those described in U.S. Pat. No. 6,905,763. Other exemplary adhesives include adhesives based on acrylic, urethane, and silicone polymers, polyurethanes, styrene block copolymers, polycarbonates, fluoropolymers, silicone rubbers, polyamides, polyesters, polyolefins, and ethyl-vinyl acetate copolymers. The adhesives are preferably able to withstand the temperatures, pressures, and moisture levels of steam sterilization processes. In some embodiments, the adhesives are moisture-permeable. In some embodiments, the adhesives are clear, transparent, or sheer. One skilled in the art can readily select adhesives appropriate for the desired use.

In some embodiments, optional lower layers 390 and optional base layers 150, 350 may include challenge layers. Challenge layers may have varying degrees of fluid permeability and modifying the environment around the moisture-indicating layer (e.g. the challenge layers may make it more difficult to dry the moisture-indicating layer and/or more difficult to wet the moisture-indicating layer). Exemplary materials for challenge layers include hydrophilic or hydrophobic materials, sponges, papers, wovens, and non-wovens. In some embodiments, hydrophilic or hydrophobic materials may be situated in close proximity to the moisture-indicating layer to create an environment around the moisture-indicating layer which is more or less humid at a given condition of humidity in the steam sterilizer chamber. Other exemplary methods for modifying the environment around the moisture-indicating layer include changing the degree of encapsulation (e.g., partial encapsulation of the moisture-indicating layer, thin layer of coating on the moisture-indicating medium, deeply embedding the moisture-indicating layer in a matrix), changing the matrix properties of the encapsulant (e.g., hydrophobicity, porosity, etc.), changing the heat capacity of the surrounding materials near the moisture-indicating layer, and changing the gas diffusion path length toward the moisture-indicating layer (e.g., placing fibrous or porous materials between the steam or water vapor source and the moisture-indicating layer, placing a long, lumen device between the steam or water vapor source and the indicator material, etc.). Exemplary materials useful in modifying the environment around the moisture-indicating layer include hydrophobic materials, hydrophilic materials, sponges, papers, medical grade papers, wovens, non-wovens, cellulose, rayon, thermoplastic polymers, a derivative of any of the foregoing materials, or a combination of any two or more of the foregoing materials.

In some embodiments, optional middle layers 380, optional lower layers 390, and optional base layers 150, 350 may include wicking layers. Wicking layers may be useful in modifying the color change behavior of the wet pack indicator with respect to the level of moisture within the enclosure or sterilization package (e.g., the wicking layers may make it easier to wet the indicator and more difficult to dry the moisture-indicating layer). Wicking layers may contain materials that readily absorb moisture from the surroundings such as hygroscopic salts. Hygroscopy of salts generally refers to the ability of the salts to attract, absorb, hold, and transport moisture from the ambient or surrounding environment. The hygroscopic salts may be employed either singly or in a mixture in accordance with the invention. Thus, a wicking layer comprising hygroscopic salt may refer to a wicking layer made of a single hygroscopic salt or mixtures of more than one hygroscopic salt. In some embodiments, the wicking layer includes a hygroscopic salt comprising an anion selected from the group comprising halide, nitrate, acetate, carbonate, and hydroxide, and comprises a cation selected from the group comprising ammonium, an alkali metal, an alkaline earth metal, and a transition metal. Exemplary hygroscopic salts for use in the wicking layers described herein include lithium bromide, lithium chloride, magnesium chloride, magnesium nitrate, sodium chloride, sodium bromide, potassium acetate, zinc bromide, cesium fluoride, zinc chloride, sodium iodide, potassium fluoride, lithium iodide, calcium bromide, sodium hydroxide, potassium hydroxide.

In some embodiments, the wet pack indicator may include a color-enhancing layer 260, 360. In some embodiments, optional middle layers 380, optional lower layers 390, and optional base layers 150, 350 may include color-enhancing layers. In some embodiments, the color-enhancing layers can have a color similar to the dry state of the moisture-indicating medium, wet state of the moisture-indicating medium, or another color. In some embodiments, the color-enhancing layer is white. The color-enhancing layers are located in close proximity to the moisture-indicating layer 120, 220, 320 such that visual comparison between the moisture-indicating layer 120, 220, 320 and the color-enhancing layer is readily accessible. For example, in some embodiments, the color-enhancing layer is disposed on top of the wet pack indicator (on the surface of the moisture-impermeable layer 110, 210, 310 opposite the first surface of the moisture-impermeable layer 110, 210, 310 upon which the moisture-indicating layer 120, 220, 320 is disposed). In some embodiments, the color-enhancing layer is disposed between the moisture-impermeable layer 110, 210, 310 and the moisture-indicating layer 120, 220, 320. In some embodiments, the color-enhancing layer is disposed on the surface of the moisture-indicating layer 120, 220, 320 opposite the moisture-impermeable layer 110, 210, 310. In some embodiments, the color enhancing layer includes a hole or transparent portion that creates a viewing area 270, 370 through which the moisture-indicating layer 120, 220, 320 remains visible. In some embodiments, the color-enhancing layer appears from the perspective of one observing the wet pack indicator (e.g. from the top of the indicator attached to a sterilization package, or from the bottom of the indicator after it has been peeled off a sterilization package) as a backing, at least a portion of which extends beyond the edges of the moisture-indicating layer 120, 220, 320 such that both the moisture-indicating layer 120, 220, 320 and the color-enhancing layer are visible. In some embodiments, the color-enhancing layer is a transparent or sheer layer comprising properties that make the color of the moisture-indicating layer 120, 220, 320 appear more intense or clear to an observer. The role of the color-enhancing layer is to provide a clearer visual indication of color change between wet and dry states of the moisture-indicating media.

The wet pack indicator is designed to be placed on the exterior of an enclosure or package to be sterilized, such that the exterior of the enclosure or package is on the side of the moisture-indicating layer 120, 220, 320 opposite the moisture-impermeable layer 110, 210, 310. While the wet pack indicator is placed on the exterior of an enclosure, it remains in fluid communication with the interior environment of the enclosure across a moisture-penetrable portion of the exterior surface of the enclosure, and thus can provide an accurate visual indication of the moisture level within the internal environmental of the enclosure. In one embodiment, a wet pack indicator is placed on the exterior of a package that includes an enclosure defining a cavity wherein the enclosure allows permeation of steam into and out of the cavity.

In another aspect of the invention, a package is provided comprising an enclosure defining a cavity. At least a portion of the enclosure comprises a moisture-permeable material. A wet pack indicator is disposed upon a surface of the moisture-permeable material. In some embodiments, the enclosure may comprise a woven or non-woven wrap, a flexible container, a rigid container comprising a venting region having a moisture-permeable filter, a peel pouch, a polymeric matrix, paper, and combinations thereof. In some embodiments, the enclosure comprises a moisture-permeable non-woven. The wet pack indicator comprises a moisture-impermeable layer and a moisture-indicating layer. The moisture-indicating layer comprises a colorimetric reversible steam-sterilization-compatible moisture-indicating medium. The moisture-impermeable layer of the wet pack indicator is peripherally bonded to a surface of the moisture-permeable material of the enclosure (e.g., a non-woven wrap or filter) such that the moisture-indicating layer is disposed between the moisture-permeable material and the moisture-impermeable layer. Surgical instruments or other medical objects such as devices and bandages may be situated within the cavity of the package. In some embodiments, the package comprises a sterilization package. Sterilization packages may comprise a flexible or a rigid enclosure, such as a flexible sterilization wrap, a flexible container, or a rigid container. Enclosure materials should be compatible with steam sterilization and maintain sterilization integrity during and after exposure to the steam sterilization process. In some embodiments, enclosure materials can comprise any material that is substantially permeable to steam and that has filtration properties sufficient to prevent the passage of pathogenic microorganisms through the enclosure. In some embodiments, enclosure materials comprise rigid enclosures. Exemplary rigid enclosures include materials such as metal, plastic, glass, ceramic, composites, a polymer, and combinations thereof. Exemplary flexible enclosures include materials made from metals, plastics, polymers, wraps, and combinations thereof. In some embodiments, the package contents, such as surgical instruments, may be contained in an interior container such as an instrument tray situated within the cavity of the enclosure.

In some embodiments, a substantial portion of the materials comprising the enclosure of the package are constructed of moisture-impermeable materials such as metal. In such embodiments, a portion of the enclosure comprises a venting region equipped with a moisture-permeable filter to allow permeation of steam into and out of the cavity within the enclosure. The filter may be integral to the container, or may be attached either on the exterior or interior of the container at the venting region by mechanical methods or by use of adhesives.

The sterilization wraps and filters can be disposable or reusable and can comprise any material that is substantially permeable to steam and that has filtration properties sufficient to prevent the passage of pathogenic microorganisms through the filter. Suitable wrap and filter materials can include medical grade paper, cellulose, rayon, polyolefins, polyesters, polyamides, polylactic acid, combinations of any of these materials, or any other filter materials known in the sterilization art. The filters can be made using a variety of processes such as lair-laying processes, wet-laid processes, melt-blowing processes, staple fiber carding and bonding processes, solution spinning processes, or other known methods of making sterilization filters.

Figure 4:
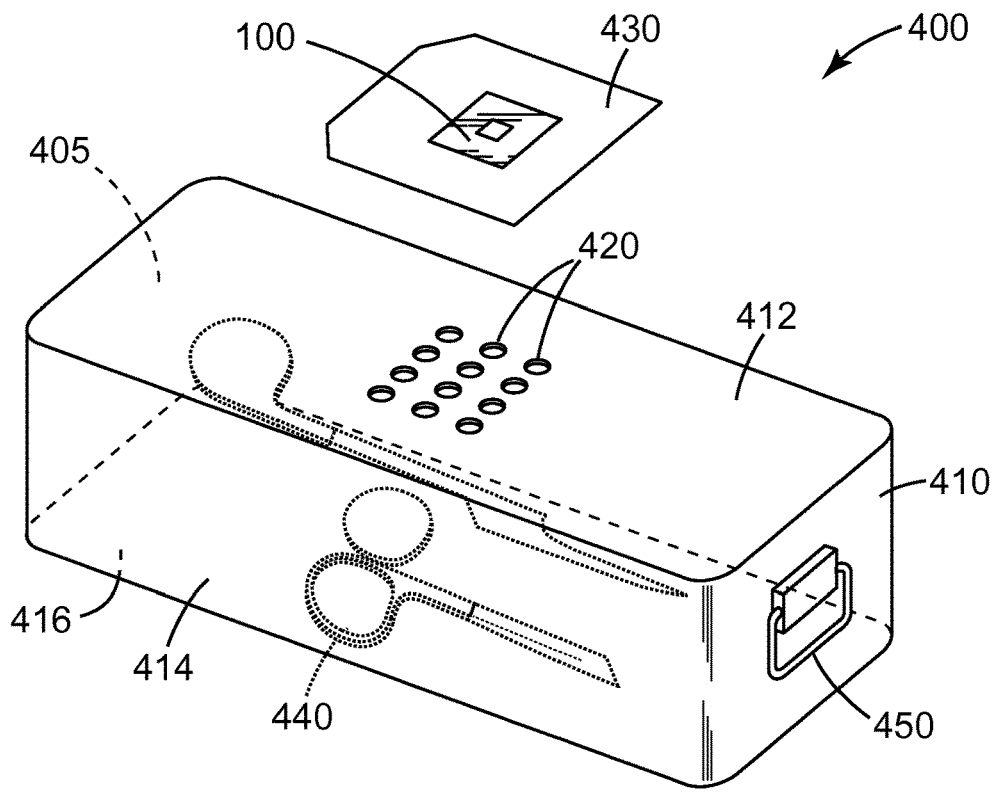
FIG. 4 is a perspective view of a package according to certain embodiments of the present disclosure.

FIG. 4 depicts a rigid sterilization package 400 comprising an enclosure 410 defining a cavity 405 and one or more venting regions 420 on the enclosure equipped with one or more moisture-permeable filters 430. The filter(s) 430 allows permeation of steam through the venting region comprising a plurality of openings 420 into and out of the cavity 405 within the package 400, while the remainder of the enclosure 410 in this embodiment is comprised of one or more moisture-impermeable materials such as steel. The sterilization package 400 comprises a top 412, bottom 416, and sidewalls 414, that together, define the interior cavity 405. In some embodiments, the container top 412 may be in the form of a lid, and in some embodiments, the container bottom 416 may be in the form of a tray. The top 412 includes a venting region comprising a plurality of openings 420. A filter 430 covers the openings 420 in the venting region. One or more wet pack indicators 100 as described herein may be disposed upon the exterior of the filter 430. Surgical instruments 440 are placed within the rigid package 400 for sterilization. Such rigid sterilization packages 400 or containers may include other components well known in the art, such as removable internal trays (not shown) for holding and transporting instruments to be sterilized. FIG. 4 shows a limited number of openings 420 in a limited venting region. However, in some embodiments, the entire rigid package 400 may be covered in openings 420 and may use multiple filters 430 or be wrapped with a sterilization wrap rather than using a filter 430.

In some embodiments, the package enclosure is flexible, such as a sterilization wrap. A sterilization wrap typically is permeable to a sterilant (e.g., steam), and the sterilization wrap typically maintains sterility of the enclosed articles (e.g. medical instruments, rigid and porous containers, instruments trays) after sterilization processing by presenting a barrier to entry of microorganisms. Flexible wraps may be reusable or disposable. Generally, cloth, linen or other woven materials fall into the reusable category and can be washed or cleaned before reuse. Disposable wraps normally include non-woven materials made from either or both natural and synthetic fibers such as paper, medical grade paper, fibrous polymeric non-wovens, and films that are capable of passing sterilants such as steam and retarding transmission of bacteria and other contaminants.

Figure 5:
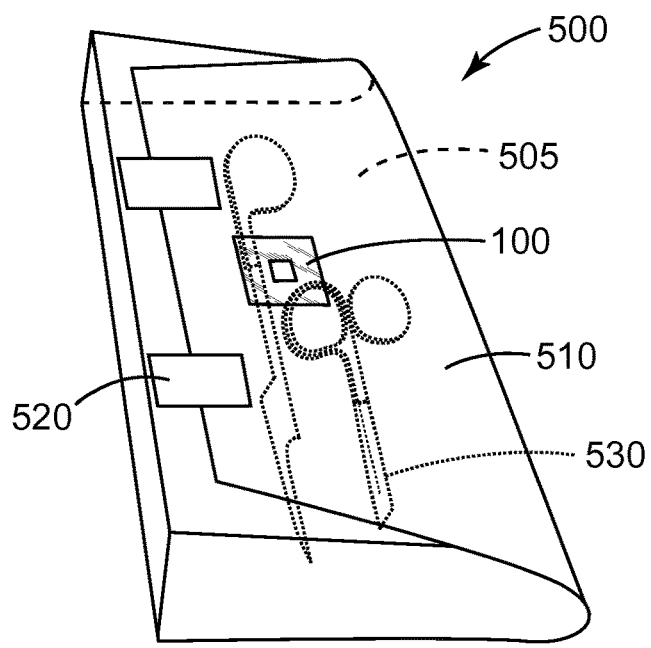
FIG. 5 is a perspective view of a package according to certain embodiments of the present disclosure.

FIG. 5 depicts a package 500 comprising a sterilization wrap enclosure 510. The package 500 comprises an enclosure (i.e. the wrap) 510 defining a cavity 505 and one or more wet pack indicators 100 as described herein disposed upon the exterior of the enclosure 510. The enclosure (i.e. the wrap) is held together by a fastener, such as adhesive strips (e.g. autoclave tape). Surgical instruments 530 are placed within the cavity 505 of the package for sterilization. In some embodiments, the surgical instruments 530 may be contained within the cavity 505 in a rigid container (not shown) having at least one venting region, or other instrument tray (not shown).

In another embodiment, a moisture-indicating article is provided, comprising a moisture-permeable material; a moisture-impermeable layer peripherally bonded to the moisture-permeable material; and a moisture-indicating layer disposed between the moisture-permeable material and the moisture-impermeable layer. The moisture-indicating layer comprises a colorimetric reversible steam-sterilization-compatible moisture-indicating medium. Other optional layers may be disposed between the moisture-impermeable layer and the moisture-indicating layer, or between the moisture-indicating layer and the moisture-permeable material. In some embodiments, the moisture-indicating article can be a sterilization wrap or a sterilization filter, pre-assembled with the at least one wet pack indicator already affixed to the exterior of the wrap or filter.

Non-woven materials suitable for use in the filters, wraps, wet pack indicator, and other articles described herein can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, polyesters, polyolefins, polyamides, many other thermoplastic materials, a derivative of any of the foregoing materials, or a combination of any two or more of the foregoing materials. The enclosure may also comprise combinations of flexible and rigid materials, such as a steel instrument tray wrapped in a non-woven wrap. Wrapping the articles (i.e. the objects to be sterilized) can be done according to conventional methods known in the art.

In some embodiments, the wet pack indicator is attached to a base layer 150, 350 or to a portion of an enclosure comprising a moisture-permeable material. Attachment of the wet pack indicator to the base layer 150, 350 or moisture-permeable material is generally facilitated through bonding by the use of adhesives, extrusion processes, ultrasonic bonding, or other appropriate attachment mechanisms know in the art. The attachment method, particularly the adhesives, should be steam-sterilization compatible. In some embodiments, the moisture-impermeable layer is peripherally bonded to the base layer 150, 350 or moisture-permeable material. By peripherally bonded it is meant that the edges 130, 230, 330 of the moisture-impermeable layer 110, 210, 310 are completely bonded to the base layer or moisture-permeable material such that the moisture-indicating layer 120, 220, 320 is completely enclosed between the moisture-impermeable layer 110, 210, 310 and the base layer 150, 350 or moisture-permeable material. It is intended that moisture reaches the moisture-indicating layer predominantly through the base layer, non-woven, or other steam-penetrable material rather than through other paths.

The wet pack indicator can be located in various positions on the enclosure. Exemplary locations include placing one or more wet pack indicators on the exterior surface of the top, bottom, or sides of the wrapped sterilization package, or on the exterior surface of a sterilization filter. In any of the above locations, the moisture-indicating layer is in fluid communication with the environment of the interior cavity of the package. The color or visible spectrum of the moisture-indicating layer is, in some embodiments, visually observable (e.g., using moisture-impermeable layers that provide sufficient transparency to allow determination of color differences in the dry and wet states of the moisture-indicating layer, or constructing the wet pack indicator such that it can be removed from the package for observation from the side opposite the moisture-impermeable layer without compromising the internal package sterility).

In some embodiments, the rigid or flexible packages or sterilization packages further comprise objects to be sterilized. The object to be sterilized can be any object that is appropriate to subject to a sterilization process. Non-limiting examples of suitable objects include surgical instruments, medical devices, dental instruments, implants, dressings, and bandages. In some embodiments, the objects to be sterilized may be placed inside the cavity of the package. In some embodiments, the objects to be sterilized may be placed inside an interior space within the cavity of a sterilization package.

The wet pack indicators, sterilization packages, and articles described herein are useful in processes for sterilizing medical objects such as surgical instruments by steam sterilization. In general, the sterilization process includes placing an enclosure or sterilization package comprising at least one wet pack indicator attached to the exterior surface of the enclosure or sterilization package into a sterilizer. In some embodiments, the sterilizer includes a sterilization chamber that can be sized to accommodate a plurality of articles to be sterilized, and can be equipped with a means of evacuating air and/or other gases from the chamber and a means for adding steam to the chamber. In some embodiments, the enclosure or package comprising the wet pack indicator can further contain objects to be sterilized, such as surgical instruments, medical devices, dental instruments, implants, dressings, and bandages.

The sterilization process further includes subjecting the enclosure or sterilization package comprising the wet pack indicator to steam sterilization. The steam can be added to the sterilization chamber after evacuating the chamber of at least a portion of any air or other gas present in the chamber. Alternatively, steam can be added to the chamber without evacuating the chamber. A series of evacuation steps can be used to assure that the steam reaches all desired areas within the chamber and contacts all desired object(s) to be sterilized, including the enclosure or sterilization package comprising the wet pack indicator and any objects inside the enclosure or package.

The steam sterilization to which the wet pack indicator and the enclosure or sterilization package are exposed may be any of the steam sterilization processes according to conventional methods known in the art, including pre-vacuum, and gravity steam sterilization processes. In at least some of the steam sterilization processes, an elevated temperature, for example, 121° C., 132° C., 134° C., 135° C., or the like, is included or may be encountered in the process. In addition, elevated pressures may be encountered, for example, 2.8 bar, or the like. Exemplary vacuum depths may include 0.8 bar, or the like. In some embodiments, steam exposure times can range from 3 minutes to 30 minutes, or the like, depending on the exposure temperatures. Exemplary drying conditions generally include post-vacuum depths of 100 mbar ($1 \times 10^4$ Pa) and other drying conditions according to conventional methods known in the art. In some embodiments, drying times can include 10 minutes, 20 minutes, 30 minutes, 40 minutes, 50 minutes, 60 minutes, or more.

Generally, once the sterilized enclosure or package is removed from the steam sterilizer, the level of moisture inside the sterilized package is determined by visually observing the color of the moisture-indicating layer of the wet pack indicator (e.g. through the transparent or sheer moisture-impermeable layer, or, if the moisture-impermeable layer is not transparent or sheer, by removing the indicator from the sterilization package and observing the moisture-indicating layer from the side opposite the moisture-impermeable layer). Other exemplary methods for determining the level of moisture in the sterilized package include observing the spectroscopic reflection or transmission of the moisture-indicating layer, or using other optical or color measurement methods such as colorimetry, reflectometry, digital imaging, and other conventional optical imaging methods. In some embodiments, where the moisture-impermeable layer is sheer or transparent, the color of the moisture-indicating layer may be observed directly without removal of the wet pack indicator from the sterilized package. Alternatively, in embodiments where the moisture-impermeable layer is solid-colored or non-transparent, or where visibility of the moisture-indicating layer through the moisture-impermeable layer has become difficult, the wet pack indicator can be removed from the exterior surface of the sterilized package and the color of the moisture-indicating layer can be viewed or measured from the bottom side (e.g. the side that was previously attached to the exterior of the sterilized package, opposite the moisture-impermeable layer).

In some embodiments, the color of the moisture-indicating layer is directly related to the current level of moisture in the environment within the inside of the enclosure or sterilized package. For example, the color of the moisture-indicating layer may be directly related to the current level of moisture in the cavity of the enclosure or package where surgical instruments are contained. By directly related, it is meant that the color of the moisture-indicating layer gives information about the level of moisture in the internal environment of the enclosure or sterilization package, or any environment in fluid communication with the moisture-indicating layer. This information may be approximate, or may be quantitatively related to the level of moisture in the environment internal environment of the enclosure or sterilization package, or any environment in fluid communication with the moisture-indicating layer. Where color is observed to determine the level of moisture, the moisture-indicating layer will, in some embodiments, exhibit a distinct color change with varying moisture conditions. For example, the moisture-indicating layer may exhibit two different colors at two different levels of relative humidity, such as appearing green at a relative humidity of 30% and appearing pink at a relative humidity of 70%. Color may be observed visually with the human eye, or with the assistance of measuring devices such as a spectrophotometer or a colorimeter. Thus, determining the level of moisture may include visually observing the color of the reversible moisture-indicating layer or measuring the visible reflection or transmission spectra of the moisture indicating medium. Moisture-indicating media that exhibit less distinct color changes may also be useful, particularly where measurement instruments are used to observe the color property of the moisture-indicating layer.

The method may further comprise the step of comparing the color of the reversible moisture-indicating layer to a predetermined threshold to determine whether the sterilized package is adequately dry. By adequately dry, it is meant that the sterilized package is dry enough to be acceptable for its intended use and for the environmental conditions of its intended use. For example, adequately dry enclosure and packages may be packages that are not considered to be wet enough to allow entrance of contaminants, such as microbes, into the enclosure or package. Another example of an adequately dry package may include a predetermined level of moisture in the internal environment of the package that corresponds to a reduced potential for condensation. For example, where the color of the moisture-indicating medium is observed, the predetermined threshold can include a certain color or a chart of colors that are indicative of certain levels of moisture at certain temperatures. The desired particular levels of moisture and temperature ranges for the predetermined threshold colors will be dependent upon the specific moisture-indicating media used, as well as the desired application in which the wet pack indicator is being used, but can be determined by those skilled in the art. Exemplary predetermined thresholds may include a certain color or other specific measurements of transparency or light intensity during absorption conventionally known in the art. In some embodiments, the predetermined thresholds are indicative of defined relative humidity values. In some embodiments, the level of moisture may correlate directly with the relative humidity of the environment. The predetermined thresholds may be determined by direct measurement, or may be generally known in the state of the art. In some embodiments, predetermined threshold colors may include green, yellow, orange, pink, blue, purple, and white. Generally, predetermined threshold values will correlate with significant changes in the color of the moisture-indicating layer, such as the level of internal package environmental moisture at which a particular moisture-indicating medium expresses a distinct color change.

Following are exemplary embodiments of methods of detecting moisture and packages used therein according to aspects of the present invention.

Embodiment 1 is a post-steam sterilization wet pack indicator comprising:

a moisture-impermeable layer having a first surface; and a moisture-indicating layer;

wherein the moisture-indicating layer comprises a reversible colorimetric steam-sterilization-compatible moisture-indicating medium;

wherein the moisture-indicating layer is disposed on or near the first surface of the moisture-impermeable layer; and wherein the moisture-indicating layer is dimensionally smaller than the moisture-impermeable layer, and the edges of the moisture-impermeable layer extend beyond the edges of the moisture-indicating layer.

Embodiment 2 is a post-steam sterilization wet pack indicator according to embodiment 1, further comprising a release liner, wherein the moisture-impermeable layer is peripherally bonded to the release liner such that the moisture indicating layer is disposed between the release liner and the moisture-impermeable layer.

Embodiment 3 is a post-steam sterilization wet pack indicator according to any one of the preceding embodiments, further comprising at least one middle layer disposed between the moisture-impermeable layer and the moisture-indicating layer.

Embodiment 4 is a post-steam sterilization wet pack indicator according embodiment 3, wherein the at least one middle layer is selected from the group consisting of an impermeable layer, an adhesive layer, and a color-enhancing layer.

Embodiment 5 is a post-steam sterilization wet pack indicator according to any one of embodiments 2-4, further comprising at least one moisture-penetrable lower layer disposed between the moisture-indicating layer and the release liner.

Embodiment 6 is a post-steam sterilization wet pack indicator according to embodiment 5, wherein the at least one moisture-penetrable lower layer is selected from the group consisting of an adhesive layer, a color-enhancing layer, a challenge layer, and a wicking layer.

Embodiment 7 is a post-steam sterilization wet pack indicator according to any one of the preceding embodiments, wherein the reversible steam-sterilization-compatible moisture-indicating medium comprises a solid support and a bis(glyoxime)-transition metal complex bound to the solid support.

Embodiment 8 is a post-steam sterilization wet pack indicator according to embodiment 7, wherein the solid support is a solid metal oxide support.

Embodiment 9 is a post-steam sterilization wet pack indicator according to embodiment 8, wherein the reversible steam-sterilization-compatible moisture-indicating medium further comprises a silyl-containing compound bound to the solid metal oxide support through a silanol bond with at least one hydroxyl group on the surface of the solid metal oxide support.

Embodiment 10 is a post-steam sterilization wet pack indicator according to any one of embodiments 1-6, wherein the reversible steam-sterilization-compatible moisture-indicating medium comprises at least one of CoCl2, CoBr2, Co(SCN)2, CuCl2, CuBr2, and combinations thereof.

Embodiment 11 is a moisture-indicating article comprising:
a moisture-permeable material;
a moisture-impermeable layer peripherally bonded to the moisture-permeable material; and
a moisture-indicating layer disposed between the moisture-permeable material and the moisture-impermeable layer;
wherein the moisture-indicating layer comprises a colorimetric reversible steam-sterilization-compatible moisture-indicating medium.

Embodiment 12 is a moisture-indicating article according to embodiment 11, further comprising at least one middle layer disposed between the moisture-impermeable layer and the moisture-indicating layer.

Embodiment 13 is a moisture-indicating article according to embodiment 12, wherein the at least one middle layer is selected from the group consisting of an impermeable layer, an adhesive layer, a wicking layer, and a color-enhancing layer.

Embodiment 14 is a moisture-indicating article according to any one of embodiments 11-13, further comprising at least one moisture-penetrable lower layer disposed between the moisture-indicating layer and the moisture-permeable material.

Embodiment 15 is a moisture-indicating article according to embodiment 14, wherein the at least one moisture-penetrable lower layer is selected from the group consisting of an adhesive layer, a color-enhancing layer, a challenge layer, and a wicking layer.

Embodiment 16 is a moisture-indicating article according to any one of embodiments 11-15, wherein the reversible steam-sterilization-compatible moisture-indicating medium comprises a solid support and a bis(glyoxime)-transition metal complex bound to the solid support.

Embodiment 17 is a moisture-indicating article according to any one of embodiments 11-15, wherein the reversible steam-sterilization-compatible moisture-indicating medium comprises at least one of CoCl2, CoBr2, Co(SCN)2, CuCl2, CuBr2, and combinations thereof.

Embodiment 18 is a moisture-indicating article according to any one of embodiments 11-17, wherein the moisture-indicating article is a sterilization wrap or a sterilization filter.

Embodiment 19 is a package comprising:
an enclosure defining a cavity, wherein at least a portion of the enclosure comprises a moisture-permeable material;
surgical instruments situated within the cavity; and
a wet pack indicator disposed upon a surface of the moisture-permeable material, wherein the indicator comprises:
a moisture-impermeable layer; and
a moisture-indicating layer comprising a colorimetric reversible steam-sterilization-compatible moisture-indicating medium;
wherein the moisture-impermeable layer of the wet pack indicator is peripherally bonded to the moisture-permeable material such that the moisture-indicating layer is disposed between the non-woven and the moisture-impermeable layer.

Embodiment 20 is a package according to embodiment 19, further comprising at least one middle layer disposed between the moisture-impermeable layer and the moisture-indicating layer.

Embodiment 21 is a package according to embodiment 20, wherein the at least one middle layer is selected from the group consisting of an impermeable layer, an adhesive layer, and a color-enhancing layer.

Embodiment 22 is a package according to any one of embodiments 19-21, further comprising at least one moisture-penetrable lower layer disposed between the moisture-indicating layer and the non-woven, wherein the at least one lower layer is moisture-penetrable.

Embodiment 23 is a package according to embodiment 22, wherein the at least one moisture-penetrable lower layer is selected from the group consisting of an adhesive layer, a color-enhancing layer, a challenge layer, and a wicking layer.

Embodiment 24 is a package according to any one of embodiments 19-23, wherein the enclosure is rigid.

Embodiment 25 is a package according to embodiment 24, wherein the enclosure comprises one or more venting regions, and wherein the enclosure comprises a moisture-permeable filter attached to the one or more venting regions.

Embodiment 26 is a package according to embodiment 25, wherein moisture-permeable filter is attached by adhesive or a mechanical attachment mechanism.

Embodiment 27 is a package according to any one of embodiments 25-26, wherein the wet pack indicator is disposed upon a surface of the filter.

Embodiment 28 is a package according to any one of embodiments 19-27, wherein the reversible steam-sterilization-compatible moisture-indicating medium comprises a solid support and a bis(glyoxime)-transition metal complex bound to the solid support.

Embodiment 29 is a package according to any one of embodiments 19-27, wherein the reversible steam-sterilization-compatible moisture-indicating medium comprises at least one of CoCl2, CoBr2, Co(SCN)2, CuCl2, CuBr2, and combinations thereof.

Embodiment 30 is a post-steam sterilization wet pack indicator comprising:
a moisture-impermeable layer having a recess; and
a moisture-indicating layer disposed within the recess;
wherein the moisture-indicating layer comprises a reversible colorimetric steam-sterilization-compatible moisture-indicating medium; and
wherein the edges of the moisture-impermeable layer extend beyond the recess.

EXAMPLES

Objects and advantages of this invention are further illustrated by the following examples, but the particular materials and amounts thereof recited in these examples, as well as other conditions and details, should not be construed to unduly limit this invention.

Example 1

Preparation of Colorimetric Moisture-Indicating Media: Ni2+/dimethylglyoxime/Al2O3

To 40.15 grams of 5 wt % aqueous solution of nickel acetate tetrahydrate (EM Science, Gibbstown, N.J.) was added 20.10 grams of BioRad AG® 7 neutral alumina microbeads, 100-200 mesh (Berkeley, Calif.). The mixture was jar rolled for 12 minutes before decanting and washing three times with deionized water. The mixture was then vacuum-filtered over a #5 WHATMAN filter paper in a Buchner funnel and further washed with deionized water.

The collected solids were dried in air at 110° C. for 15 minutes. The hot beads were quickly transferred (within 20 seconds of removal from the oven) directly into a basic dimethylglyoxime aqueous solution (formulation: 0.12 grams dimethylglyoxime (Mallinckrodt Chemical Works, New York, N.Y.), 11.58 grams 1 M aqueous solution of potassium hydroxide (BDH Chemicals, West Chester, Pa.), 28.37 grams deionized water). The beads rapidly changed to a bright pink color, along with the formation of residual red/pink colored material and pink solution. After two minutes of mixing, the mixture was decanted and washed with deionized water at three times to remove most of the residuals. The mixture was then vacuum-filtered over a #5 WHATMAN filter paper in a Buchner funnel, and further washed with deionized water. The collected solids were dried in air at 110° C. for 70 minutes. The dried solids were pale yellow in color.

Construction of Wet Pack Indicator

The wet pack indicator (WPI) was prepared in the following manner. A piece of transparent polypropylene film tape (SCOTCH 3750 Commercial Performance Packaging Tape, available from 3M Company of St. Paul, Minn., USA) was cut to a 1 centimeter square size and then manually coated with particles of the colorimetric moisture-indicating media prepared above. The tape was completely covered so that an approximate monolayer of particles was adhered to the pressure sensitive adhesive (PSA) side of the one centimeter square piece of tape. This coated piece of tape was then centered and placed on a second larger square piece of the same type of tape, such that the PSA side of the second piece of tape contacted the polypropylene backing of the first piece of tape. The second square piece of tape was approximately 2.5 centimeters on each side, 6.25 square centimeters in total area. This created a "PSA border" with a width of about 0.75 centimeters around the first piece of tape coated with colorimetric moisture-indicating media. A release liner was obtained by taking the release liner from a sheet of AVERY White Full-Sheet Shipping Labels for Laser Printers 5165, available from Avery Dennison of Pasadena, Calif., USA, and cutting it to size, 2.5 cm×2.5 cm square to fit the second square piece of tape. The release liner was placed over the exposed PSA of the second piece of tape and also covered the colorimetric moisture-indicating media of the first piece of tape. The SCOTCH 3750 Commercial Performance Packaging Tape was selected for its high temperature durability. The tape was also selected because the adhesive was robust enough to withstand the humidity, temperature and pressure conditions in the steam sterilizer without significant delamination. The release liner is removed prior to placing the WPI onto the outer surface of the sterilization package wrap or filter surface, described below.

The construction of the WPI as described ensures that the film covering the media is less steam/water vapor permeable than the sterilization fabric upon which it is intended to be placed. This construction required the steam/water vapor to reach the media under the carrier tape by first passing through the wrap fabric and into the inner cavity of the package and then passing back through the wrap fabric under the location of the colorimetric moisture-indicating media. In this way the level of humidity which the media was indicating was related to the humidity level within the packaging inner cavity.

Steam Sterilization Conditions

A steam sterilizer (GETINGE Model 410 AC1 obtained from Getinge USA, Inc. of Rochester, N.Y.) was employed to test the WPI under simulated Dry Load and induced Wet Load conditions at 135° C. Three cycles of vacuum pulses were used before sterilization. The exposure time to steam at 135° C. was 3 minutes. For the Dry Load, the post vacuum depth was 32.8 kPa (0.328 bar), and the drying time was 40 minutes. For the Wet Load the post vacuum depth was 90 kPa (0.9 bar) and the drying time was 1 second.

TABLE 1A

Programmed Process Conditions for Steam Sterilization
Equipment: Getinge 410 AC1
Cycle: 135° C./275° F. 3-min Pre-vacuum (dynamic air removal)

| | |
|---|---|
| PREVACUUM PULSES | 3 |
| PULS 1 + LVL | 2.200 BAR (220 kPa) |
| PULS 2 + LVL | 2.200 BAR |
| PULS 3 + LVL | 2.200 BAR |
| PULS 1 − LVL | 0.333 BAR (33.3 kPa) |
| PULS 2 − LVL | 0.667 BAR (66.7 kPa) |
| PULS 3 − LVL | 0.667 BAR |
| VAC HOLD TM (h:mm:ss) | 0:00:00 |
| EVAC RAMP REG | 0.710/M |
| STEAM PRESS REG | 0.710/M |
| STERILIZE REG | 85.0/M |
| EXPOSURE TEMP | 135.0° C. |
| EXPOSURE TIME (h:mm:ss) | 0:03:00 |
| EXPOSURE F0 | 10 |

TABLE 1B

Final Cycles: Dry Load vs. Wet Load Process Conditions

| Process Condition | DRY CYCLE | WET CYCLE |
|---|---|---|
| POST VACUUM DEPTH | 32.8 kPa (0.328 BAR) | 90 kPa (0.9 BAR) |
| DRYING TIMER (h:mm:ss) | 0:40:00 | 0:00:01 |

Sterilization Containers

Two types of sterilization packaged containers were used in these experiments. Container A was a 3M M306 AUTOCLAVE CASE, a perforated hinged lid stainless steel case with handles and internal tray dimensions of 36.4×22.2×9.4 centimeters (14.25×8.75×3.75 inches), available from 3M Company of St. Paul, Minn., USA. Container A was filled with stainless steel medical instruments, and was completely wrapped with a blue non-woven sterilization wrap, KIM-GUARD ONE STEP STERILIZATION WRAP KC400, available from Kimberly-Clark of Irving, Tex. Each sheet of the KC400 wrap is actually two sheets of SMS fabric bonded together on the edges. Container B was a V. Mueller Genesis Sterilization Container with dimensions 28×58×15 centimeters (11×23×6 inches), made of anodized aluminum. Container B also had 4 flat, built-in filter compartments, 2 each on the top and on the bottom of the container. One sheet of the KC400 wrap was pulled apart into two separate sheets of SMS material. This single SMS sheet was cut to size and used as the filter material for the 4 filter compartments of Container B.

Use of the WPI

For each WPI, the liner was removed and the WPI was applied to the target location, making certain that the adhesive border was well sealed around the edges of the indicator media. The WPI was adhered to the outer surface of the KC400 sterilization wrap on Container A and on the outer facing surface of the SMS filter material used for Container B. The WPIs were placed in the following specific locations. Two WPIs were placed on the bottom, and one on the side of the wrapped Container A. One WPI was placed on each of the 4 filters placed into the 4 built-in filter compartments of Container B, two each on the top and the bottom of Container B. Container A was placed on the top shelf of the two shelf autoclave chamber, and Container B was placed on the bottom shelf. The two packages were placed into the steam sterilizer and exposed to the steam sterilization treatment conditions described above for Dry Load. Two additional, identical packages were prepared in the same manner and subjected to the Wet Load process conditions. The packages were removed from the sterilizer and the color of each of the WPIs was visually examined to determine the level of moisture remaining in the package after the sterilization treatment.

Example 1

Results

For all results, a visual observation of the color of the WPI was made before and after the exposure to the Dry Load or Wet Load steam sterilization process cycles. The term "pale" was used to indicate a visual perception of a relatively lighter or less saturated version of the color observed. For example, the result "pale yellow" would be considered a relatively lighter version of yellow; or a less saturated yellow. Likewise, "pale pink" would be considered a relatively lighter version of pink; or a less saturated pink. The color pink itself is generally regarded as a lighter version of the color red; or a less saturated red, since, for example, the mixing of red paint and white paint results in a paint of the color pink. Before being exposed to any moisture, each dry WPI appeared pale yellow in color. When saturated with water, the WPI turned pink in color.

TABLE 2

Dry Load Container A

| Condition | Side site #1 | Bottom site #1 | Bottom site #2 |
| --- | --- | --- | --- |
| Before Sterilization | Pale yellow | Pale yellow | Pale yellow |
| After Sterilization | Pale yellow | Pale pink | Pink |

After exposure to Dry Load sterilization conditions, Container A appeared to have liquid water remaining between the bottom of the metal container and the inner wrap surface, leading to the pink coloration of the WPI placed at the bottom of the packaging. However, the WPI at the side of the package indicated a dry package. Therefore, correct placement of the WPI is important depending on the indication level desired. Given the process conditions used, apparently even 40 minutes of drying time was not enough to evaporate all moisture from inside wrap (container). The WPI successfully indicated the moisture environments inside the wrap even though the WPI were attached to the outside of the wrap.

TABLE 3

Dry Load Container B

| Condition | Top site #1 | Top site #2 | Bottom site #1 | Bottom site #2 |
| --- | --- | --- | --- | --- |
| Before Sterilization | Pale yellow | Pale yellow | Pale yellow | Pale yellow |
| After Sterilization | Pale yellow | Pale yellow | Pale yellow | Pale yellow |

After exposing Container B to Dry Load sterilization conditions, the exterior and the interior of the container including the filter appeared completely dry. Each WPI also appeared pale yellow after sterilization, indicating a dry package. Prior to exposure to the steam sterilization conditions the prepared WPI all appeared pale yellow in color. As a verification of the indicator's ability to sense moisture, after exposure to the steam sterilization conditions, one WPI was intentionally spiked with a small amount of water and immediately turned from pale yellow to an intense pink color.

TABLE 4

Wet Load Wrapped Container A

| Condition | Side site #1 | Bottom site #1 | Bottom site #2 |
| --- | --- | --- | --- |
| Before Sterilization | Pale yellow | Pale yellow | Pale yellow |
| After Sterilization | Pale orange | Pale Pink | Pink |

After exposing Container A to Wet Load sterilization conditions, the wrap on the bottom side of the container had severe moisture condensation even though no moisture condensation was observed on the side of the container. The color of the WPIs changed from pale yellow (which was before sterilization) to pale orange for the side site, and to pale pink and pink for the two bottom sites, indicating an increasing amount of moisture detected at different locations around Container A.

TABLE 5

Wet Load Container B

| Condition | Top site #1 | Top site #2 | Bottom site #1 | Bottom site #2 |
| --- | --- | --- | --- | --- |
| Before Sterilization | Pale yellow | Pale yellow | Pale yellow | Pale yellow |
| After Sterilization | Pink | Pink | Pink | Pink |

After exposing Container B to Wet Load sterilization conditions, the container was opened and pooled water was observed inside at the bottom of Container B. The pink color of the WPIs accurately indicated this wet condition.

What is claimed is:
1. A moisture-indicating article comprising:
a moisture-permeable material;
a moisture-impermeable layer peripherally bonded to the moisture-permeable material;
a moisture-indicating layer disposed between the moisture-permeable material and the moisture-impermeable layer; and
a color-enhancing layer located proximate the moisture-indicating layer such that a visual comparison between the color-enhancing layer and the moisture-indicating layer can be made;
wherein the moisture-indicating layer comprises a colorimetric reversible steam-sterilization-compatible moisture-indicating medium comprising a solid metal oxide support, a bis-glyoxime-transition metal complex bound to the solid metal oxide support, and a silyl-containing compound bound to the solid metal oxide support through a silanol bond with at least one hydroxyl group on the surface of the solid metal oxide support.

2. The moisture-indicating article of claim 1, further comprising at least one middle layer disposed between the moisture-impermeable layer and the moisture-indicating layer.

3. The moisture-indicating article of claim 2, wherein the at least one middle layer is selected from the group consisting of an impermeable layer, an adhesive layer, and a wicking layer, and the color-enhancing layer.

4. The moisture-indicating article of claim 1, further comprising at least one moisture-penetrable lower layer disposed between the moisture-indicating layer and the moisture-permeable material.

5. The moisture-indicating article of claim 4, wherein the at least one moisture-penetrable lower layer is selected from the group consisting of an adhesive layer, a color-enhancing layer, a challenge layer, and a wicking layer.

6. A post-steam sterilization wet pack indicator comprising:
   a moisture-impermeable layer having a recess; and
   a moisture-indicating layer disposed within the recess;
   wherein the moisture-indicating layer comprises a reversible colorimetric steam-sterilization-compatible moisture-indicating medium comprising a solid metal oxide support, a bis-glyoxime-transition metal complex bound to the solid metal oxide support, and a silyl-containing compound bound to the solid metal oxide support through a silanol bond with at least one hydroxyl group on the surface of the solid metal oxide support; and
   wherein the edges of the moisture-impermeable layer extend beyond the recess.

7. The moisture-indicating article of claim 1, wherein the moisture-indicating layer is a first color when the moisture-indicating layer is in a dry state, wherein the moisture-indicating layer is a second color when the moisture-indicating layer is in a wet state, wherein the color-enhancing layer is a third color, wherein the first color and the third color are the same color.

8. The moisture-indicating article of claim 1, wherein the moisture-indicating layer is a first color when the moisture-indicating layer is in a dry state, wherein the moisture-indicating layer is a second color when the moisture-indicating layer is in a wet state, wherein the color-enhancing layer is a third color, wherein the second color and the third color are the same color.

9. The moisture-indicating article of claim 1, wherein the moisture-impermeable layer has a first surface, wherein the color-enhancing layer is disposed on a surface of the moisture-impermeable layer opposite the first surface.

10. The moisture-indicating article of claim 1, wherein the color-enhancing layer is disposed between the moisture-impermeable layer and the moisture-indicating layer.

11. The moisture-indicating article of claim 1, wherein the color-enhancing layer comprises a hole or transparent portion that creates a viewing area through which the moisture-indicating layer can be viewed.

12. The moisture-indicating article of claim 1, wherein the silyl-containing compound is hydrophobic.

13. The post-steam sterilization wet pack indicator of claim 6, wherein the silyl-containing compound is hydrophobic.

* * * * *